United States Patent
Perlberg et al.

(10) Patent No.: US 9,006,431 B2
(45) Date of Patent: Apr. 14, 2015

(54) CRYSTALLINE FORM OF PEMIROLAST

(71) Applicant: Cardoz AB, Stockholm (SE)

(72) Inventors: Anett Perlberg, Gunzgen (CH); Martin Viertelhaus, Constance (DE); Ulrika Rosenström, Stockholm (SE); Karol Horvath, Södertälje (SE)

(73) Assignee: RSPR Pharma AB, Stockholm (SE)

( * ) Notice: Subject to any disclaimer, the term of this patent is extended or adjusted under 35 U.S.C. 154(b) by 0 days.

(21) Appl. No.: 14/274,951

(22) Filed: May 12, 2014

(65) Prior Publication Data

US 2014/0329839 A1 Nov. 6, 2014

Related U.S. Application Data

(63) Continuation of application No. 13/378,787, filed as application No. PCT/GB2010/001168 on Jun. 15, 2010, now abandoned.

(60) Provisional application No. 61/187,355, filed on Jun. 16, 2009, provisional application No. 61/187,348, filed on Jun. 16, 2009.

(51) Int. Cl.
| | |
|---|---|
| C07D 239/70 | (2006.01) |
| C07D 471/04 | (2006.01) |
| A61K 31/519 | (2006.01) |
| A61K 45/06 | (2006.01) |

(52) U.S. Cl.
CPC ............ C07D 471/04 (2013.01); A61K 31/519 (2013.01); A61K 45/06 (2013.01)

(58) Field of Classification Search
CPC ........................... C07D 471/04; C07D 487/04
USPC .......................................... 544/282; 514/250
See application file for complete search history.

(56) References Cited

U.S. PATENT DOCUMENTS 4,122,274 A * 10/1978 Juby .............................. 544/282

FOREIGN PATENT DOCUMENTS

| EP | 0 316 174 | 5/1989 |
|---|---|---|
| EP | 1 285 921 | 2/2003 |
| JP | 03-074385 | 3/1991 |
| WO | 2008/074975 | 6/2008 |
| WO | 2008/075028 | 6/2008 |

OTHER PUBLICATIONS

Tanaka, "Permirolast Potassium," Drugs of Today, vol. 28, No. 1, pp. 29-31 (1992).
Yanagihara et al., "Immunopharmacologial Studies on TBX, a New Antialleric Drug (4) Effects on Type II to Type IV Allergic Reactions and Immunological Functions in Animal Models," Japan J. Pharmacol., vol. 51, pp. 93-100 (1989).
Standard Commodity Classification No. 87449, Document translated from Japanese for Cardoz by Japan Science and Technology Agency "Antiallergic agent—Alegysal tablet 5 mg—Alegysal tablet 10 mg—Alegysal dry syrup," Pharmaceutical Interview Form (IF), pp. 1-64, Revised in Oct. 2007 (7th version) (English Translation).
Kinbara et al., "Plasma Level and Urinary Excretion of TBX in Humans," Japanese Pharmacology & Therapeutics, vol. 18, No. 3, pp. 183(1035)-188(1040) (1990) (English Translation).
Gyires, K. et al., "The Effect of Some Anti-Ulcer Agents on the Early Vascular Injury of Gastric Mucosa Induced by Ethanol," Acta Physiologica Hungarica, vol. 73 (2-3), pp. 149-154 (1989).
Vogel, Arthur I., Vogel's Textbook of Practical Organic Chemistry including Qualitative Organic Analysis, 4th Edition, Longman Group Limited London, pp. 105-124 (1978).
Chayvialle, A. Pfeiffer et al., Gastroenterology, vol. 88, No. 5, Part 2, p. 1359 (1985).
Cotton and Wilkinson, Advanced Inorganic Chemistry, A Comprehensive Text, 4th Edition, John Wiley & Sons, Inc., pp. 261-263 (1980).
The International Search Report of PCT/GB2010/001168 dated Dec. 10, 2010.
The International Preliminary Report on Patentability dated Dec. 16, 2011.

* cited by examiner

*Primary Examiner* — Sudhakar Katakam
(74) *Attorney, Agent, or Firm* — McDonnell Boehnen Hulbert & Berghoff LLP

(57) ABSTRACT

There is provided a hemihydrate form of the sodium salt of pemirolast.

13 Claims, 8 Drawing Sheets

CRYSTALLINE FORM OF PEMIROLAST

This application is a continuation application of U.S. patent application No. 13/378,787, filed Mar. 6, 2012, which in turn is the National Stage of and claims priority to International Application No. PCT/GB2010/001168, filed Jun. 15, 2010, which claims benefit to U.S. provisional Application No. 61/187,355, filed on Jun. 16, 2009 and U.S. provisional Application No. 61/187,348, filed on Jun. 16, 2009, all of which are incorporated by reference in their entirety.

FIELD OF THE INVENTION

This invention relates to new solid state forms of a drug, to pharmaceutical compositions containing them, and to processes for obtaining them.

BACKGROUND TO THE INVENTION

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations comprising the active compound.

Chemical stability, solid state stability, and "shelf life" of the active ingredients are also very important factors. The drug substance, and compositions containing it, should be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

Amorphous, or semi-amorphous materials may present significant problems in this regard. For example, such materials are typically difficult to handle and to formulate, provide for unreliable solubility, and are often found to be unstable and chemically impure.

The skilled person will appreciate that, if a drug can be readily obtained in a stable crystalline form, the above problems may be solved.

Further, crystalline drug compounds have been shown to provide more reliable and reproducible plasma concentration profiles following administration to a patient.

Thus, in the manufacture of commercially viable, and pharmaceutically acceptable, drug compositions, it is important, wherever possible, to provide drug in a substantially crystalline, and stable, form.

It is to be noted, however, that this goal is not always achievable. Indeed, typically, it is not possible to predict, from molecular structure alone, what the crystallisation behaviour of a compound will be. This can usually only be determined empirically.

Pemirolast is an orally-active anti-allergic drug which is used in the treatment of conditions such as asthma, allergic rhinitis and conjunctivitis. See, for example, U.S. Pat. No. 4,122,274, European Patent Applications EP 316 174 and EP 1 285 921, Yanagihara et al, *Japanese Journal of Pharmacology*, 51, 93 (1989) and *Drugs of Today*, 28, 29 (1992). The drug is presently marketed in e.g. Japan as the potassium salt under the trademark ALEGYSAL™.

Commercial pemirolast potassium has the disadvantage that it is known to give rise to sharp plasma concentration peaks in humans (see, for example, Kinbara et al, "*Plasma Level and Urinary Excretion of TBX in Humans*", *Japanese Pharmacology & Therapeutics*, 18(3) (1990), and "*Antiallergic agent—ALEGYSAL tablet 5 mg—ALEGYSAL tablet 10 mg—ALEGYSAL dry syrup*", Pharmaceutical Interview Form (IF), Revised in October 2007 (7th version), Standard Commodity Classification No.: 87449). The latter document also reports that the potassium salt of pemirolast is hygroscopic, which is believed to give rise to chemical instability, and possesses a bitter taste.

U.S. Pat. No. 4,122,274 describes a process for the production of salts of pemirolast, including potassium salts and (at Example 14) a sodium salt. As described herein, this technique produces a sodium salt that is physically unstable. Sodium salts of pemirolast are also mentioned (but a synthesis thereof not described) in international patent applications WO 2008/074975 and WO 2008/075028.

We have now found that it is possible to produce a stable, crystalline sodium salt of pemirolast and also, unexpectedly, that such a salt is less soluble in aqueous media, and less hygroscopic, than corresponding prior art potassium salts of pemirolast. Such salts are thus expected not to give rise to the sharp plasma concentration peaks, nor the poor taste and hygroscopicity problems mentioned above for pemirolast potassium.

DISCLOSURE OF THE INVENTION

According to a first aspect of the invention there is provided a hemihydrate form of the sodium salt of pemirolast (hereinafter referred to as "the compounds of the invention"). Compounds of the invention may, in the alternative, be referred to as "pemirolast sodium hemihydrate(s)".

There is further provided a sodium salt of pemirolast, and/or a compound of the invention, that contains at least about 0.3, preferably at least about 0.35 and more preferably at least about 0.4 moles, and/or no more than about 0.7, preferably no more than about 0.65 and more preferably no more than about 0.6 moles, of water (such as about 0.5 moles of water), per mole of pemirolast, whether such water is tightly bound or loosely bound (i.e. crystal water or otherwise) or not.

We have found that compounds of the invention may be readily obtained in forms that are substantially crystalline in nature.

Although it is possible to produce compounds of the invention in forms which are greater than about 98%, such as about 95% crystalline, by "substantially crystalline" we include greater than about 60%, preferably greater than about 75%, and more preferably greater than about 80% (such as about 90%) crystalline. The degree (%) of crystallinity may be determined by the skilled person using powder X-ray diffraction (PXRD). Other techniques, such as solid state NMR, FT-IR, Raman spectroscopy, differential scanning calorimetry (DSC) microcalorimetry, and calculations of the true density, may also be used.

Preferred compounds of the invention may be characterised by a powder X-ray diffraction pattern comprising a characteristic crystalline peak with a 2-Theta value (in degrees) of around (i.e. at about or at approximately) 26.6 (which is around 26.5 in FIG. 1/Table 2), and preferably also comprising a further strong crystalline peak with a 2-Theta value (in degrees) of around (i.e. at about or at approximately) 25.3 (which is around 25.2 in FIG. 1/Table 2). More preferably compounds of the invention may be characterised by a powder X-ray diffraction pattern comprising additional strong crystalline peaks with 2-Theta values (in degrees) of around (i.e. at about or at approximately) 13.0 (around 12.9 in FIG. 1/Table 2), 15.3 (around 15.2 in FIG. 1/Table 2), 18.2 (around 18.1 in FIG. 1/Table 2) and/or 28.4 (around 28.3 in FIG. 1/Table 2); more preferably comprising further strong crystalline peaks with 2-Theta values (in degrees) of around (i.e. at about or at approximately) 16.8 (around 16.7 in FIG. 1/Table 2), 19.2 (around 19.1 in FIG. 1/Table 2) and/or 27.0 (around 26.9 in FIG. 1/Table 2); and more preferably comprising further strong crystalline peaks with 2-Theta values (in degrees) of around (i.e. at about or at approximately) 14.9 and/or 29.5.

Preferred compounds of the invention may also be characterised by a powder X-ray diffraction pattern that is essentially according to that shown in FIG. 5 (and/or FIG. 1) attached hereto and/or as tabulated in Table 4 (and/or Table 2) hereinafter. The skilled person will appreciate that a form of pemirolast sodium hemihydrate shows "essentially" the same powder X-ray diffraction pattern as another when it was clear to that skilled person from the respective patterns (i.e. the relative spacing of the peaks, allowing for experimental error, such as preferred orientation of the sample and respective instrument settings (e.g. apparatus type, standardization and/or calibration)) that the same crystalline form has been formed (as is the case between the forms characterized by FIG. 5 and Table 4, and FIG. 1 and Table 2, respectively). Thus, limits of experimental error for d-values as specified herein may be in the range ±2 or thereabouts on the last decimal place.

Compounds of the invention are preferably substantially crystallographically pure. By "substantially crystallographically pure" we include a crystalline form of pemirolast sodium hemihydrate that, as far as can be judged by PXRD measurements, contains less than about 5%, more preferably less than about 3% and especially less than about 1% of other crystalline forms of pemirolast sodium (whether in the form of hemihydrate or otherwise, and as judged by the presence of PXRD peaks from such other crystalline forms).

We have found that the compounds of the invention have a surprisingly improved physical and/or chemical stability when compared with other forms of sodium salts of pemirolast, including those prepared as described in U.S. Pat. No. 4,122,274.

The term "stable" as defined herein includes chemical stability and solid state stability.

By "chemical stability", we include that the compound can be stored in an isolated solid form, or in the form of a solid formulation in which it may be provided in admixture with pharmaceutically acceptable carriers, diluents or adjuvants, under normal storage conditions, with an insignificant degree of chemical degradation or decomposition.

By "solid state stability", we include that the compound can be stored in an isolated solid form, or in the form of a solid formulation in which it may be provided in admixture with pharmaceutically acceptable carriers, diluents or adjuvants, under normal storage conditions, with an insignificant degree of solid state transformation (e.g. crystallisation, recrystallisation, loss of crystallinity, solid state phase transition, hydration, dehydration, solvatisation or desolvatisation).

Examples of "normal storage conditions" include temperatures of between minus 80 and plus 50° C. (preferably between 0 and 40° C. and more preferably ambient temperature, such as between 15 and 30° C.), pressures of between 0.1 and 2 bars (preferably atmospheric pressure), and/or exposure to 460 lux of UV/visible light, for prolonged periods (i.e. greater than or equal to six months). Under such conditions, compounds of the invention may be found to be less than about 15%, more preferably less than about 10%, and especially less than about 5%, chemically degraded/decomposed, or solid-state transformed, as appropriate. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

The term "normal storage conditions" may also include relative humidities of between 5 and 95% (preferably 10 to 60%). However, in the case of certain crystalline forms according to the invention, changes in conformation or crystal structure by hydration and/or dehydration may occur as a result of prolonged exposure to certain extremes of relative humidities, at normal temperatures/pressures.

We have found that it is possible to obtain compounds of the invention via crystallisation advantageously following at least partial dissolution and/or suspension of a sodium salt of pemirolast.

In this respect, compounds of the invention may be obtained advantageously by reacting pemirolast with a sodium-containing base, followed by crystallisation from an appropriate solvent system. Pemirolast sodium may be isolated prior to said crystallisation.

The sodium-containing base needs to be basic enough to remove a proton from the tetrazole moiety in the pemirolast molecule. Preferred bases thus include sodium hydroxide, as well as sodium hydride, sodium amide and sodium alkoxides. Sodium alkoxides that may be mentioned include $C_{1-6}$ alkoxides of sodium, such as $C_{1-4}$, e.g. $C_{1-3}$, alkoxides, for example sodium ethoxide, or for example sodium methoxide.

Crystallisation of compounds of the invention from an appropriate solvent system may be achieved by attaining supersaturation in a solvent system which comprises a sodium salt of pemirolast (e.g. by cooling, by solvent evaporation, and/or via the addition of a suitable antisolvent). Crystallisation may also be effected by decreasing the solubility of the substance by the addition of a sodium salt to increase the ion strength of the solution (such as NaCl or $NaSO_4$; so-called "salting out"), and/or the addition of seed crystals (once available) to a supersaturated solution.

The solvent system may include one or more organic solvents, such as alkyl acetates (e.g. linear or branched $C_{1-6}$ alkyl acetates, such as ethyl acetate, iso-propyl acetate and butyl acetate), lower (e.g. linear or branched $C_{1-6}$, preferably $C_{1-4}$) alkyl alcohols (e.g. methanol, ethanol, iso-propanol), aliphatic and aromatic hydrocarbons (e.g. iso-octane, n-heptane and toluene), dialkyl ketones (e.g. methyl ethyl ketone, acetone and methyl iso-butyl ketone), dialkyl ethers (e.g. di-iso-propyl ether and tert-butyl methyl ether), cyclic ethers (e.g. tetrahydrofuran and dioxane) acetonitrile and dimethylformamide. Mixtures of any of the above-mentioned solvents may be used. Organic solvents may contain water.

Different crystalline forms may have different solubilities in different organic solvents at any given temperature. In this respect, above-mentioned, or other, solvents may be employed as "antisolvents" (i.e. a solvent in which compounds of the invention are poorly soluble, such as methanol, ethanol, or isopropanol, but which is miscible with another solvent, in which compounds of the invention are more soluble, such as water), and may thus aid the crystallisation process.

Particularly suitable solvents include lower alkyl alcohols (e.g. $C_{1-4}$ alcohols, such as isopropanol, preferably methanol or more preferably ethanol) which may be in admixture with a small amount of water.

In particular, we have found that compounds of the invention may be obtained by way of crystallisation following partial dissolution (also known as equilibration and/or slurry formation) of pemirolast sodium in the presence of an organic solvent (e.g. a lower alkyl alcohol, such as ethanol), in the further presence of no more than about 12% (w/w, as a proportion of the organic solvent), particularly no more than about 11%, and especially no more than about 10% (e.g. less than about 8%, such as less than about 5%, e.g. less than about 3%) of water. Such water may be added to the crystallisation mixture or may already be present in one or both of the organic solvent or the pemirolast sodium that is to be crystallised. The skilled person will nonetheless appreciate that this crystallisation may not be performed under completely anhydrous conditions, as it is necessary to have some water present in the system to form a hemihydrate. The skilled person will also appreciate that partial dissolution is not complete dissolution (e.g. to form a saturated solution) and therefore that this process does not comprise a standard recrystallisation. This process is also preferably carried out at temperatures of less than about 75° C., such as about 72°, e.g. about 70° C.

We have also found that compounds of the invention may be obtained by way of:

(a) crystallisation following partial dissolution (equilibration and/or slurry formation) of pemirolast sodium in an aqueous solvent (i.e. comprising at least about 95% (w/w) water, such as pure water) at above about 70° C., e.g. about 72° C., such as about 75° C., and for example at about 80° C. or above. This process is also not a recrystallisation and preferably comprises filtration at the aforementioned temperature(s) to isolate the formed crystals; and (b) complete (e.g. at least about 95%) dissolution of pemirolast sodium in an aqueous solvent (i.e. comprising at least about 95% (w/w) water, such as pure water) followed by addition of an excess of antisolvent (e.g. ethanol). This process preferably comprises addition of the antisolvent at a high temperature (e.g. around the boiling point of the solvent). For ethanol, this is about 70° C. (e.g. about 72° C.) to about 80° C., such as about 75° C.) and cooling to a lower temperature (e.g. room temperature, such as about 20° C.) prior to isolation of the crystals.

The skilled person will appreciate that the concentration in solution (and/or partial solution) of the compound that is to be crystallised, and the solvent system that is used, may influence crystallisation temperatures and crystallisation times.

As may be appreciated by the skilled person, the crystalline form that is obtained depends upon both the kinetics and the thermodynamics of the crystallisation process. Under certain thermodynamic conditions (solvent system, temperature, pressure and concentration of the compound of the invention), one crystalline form may be more stable than another (or indeed any other). However, other crystalline forms that may have, in comparison, a relatively low thermodynamic stability, may be kinetically-favoured. Thus, in addition, kinetic factors, such as time, impurity profile, agitation, the presence of seeds, etc. may also influence which forms appear. Thus, the procedures discussed herein may be adapted by the skilled person as appropriate in order to obtain pemirolast sodium hemihydrate(s) and indeed (if appropriate) different crystalline forms of hemihydrate forms of sodium salts of pemirolast.

In order to ensure that crystalline forms as described herein are prepared in the absence of other crystalline forms, crystallisations may be carried out by seeding with nuclei and/or seed crystals of the desired crystalline form in the absence of nuclei and/or seed crystals of other crystalline forms.

Further, drying temperature and drying time may affect the solid state properties and/or the solid state form of compounds of the invention. For example, dehydration may occur at low humidities and/or elevated temperatures and/or reduced pressure. For example, following the formation of a crystalline hemihydrate, there may be a critical humidity level below which drying may be performed, which may result in crystal water being lost, and at least a partial solid state transformation to an anhydrate occurring.

This notwithstanding, compounds of the invention may also be formed by dehydration of a higher hydrate (e.g. a heptahydrate) of pemirolast sodium, for example as described hereinafter.

The preparation, and characterisation, of compounds of the invention, are described hereinafter. Different crystalline forms of the compounds of the invention may be readily characterised using powder X-ray diffraction (PXRD) methods, for example as described hereinafter.

Compounds of the invention may be isolated using techniques which are well known to those skilled in the art, for example decanting, filtering and/or centrifuging.

We have found that, by employing the crystallisation processes described herein, it is possible to produce compounds of the invention with a high chemical purity.

When compounds of the invention are crystallised as described herein, the resultant compound is in a form which has improved chemical and solid state stability, as mentioned hereinbefore, as well as improved solubility and hygroscopicity profiles when compared to other salts of pemirolast, and/or other forms of sodium salts of pemirolast.

Pharmaceutical Preparations and Medical Use

The compounds of the invention are useful because they possess pharmacological activity. They are therefore indicated as pharmaceuticals.

In particular, the compounds of the invention find utility in the treatment of inflammatory conditions.

Inflammatory conditions are typically characterized by activation of immune defence mechanisms, resulting in an effect that is more harmful than beneficial to the host. Such conditions are generally associated with varying degrees of tissue redness or hyperemia, swelling, hyperthermia, pain, itching, cell death and tissue destruction, cell proliferation, and/or loss of function. Inflammatory conditions that may be mentioned include arteritis, diabetes mellitus (including Type 1 diabetes and, preferably, Type 2 diabetes), obesity, metabolic syndrome, endometriosis, allergy (including allergic conjunctivitis and allergic rhinitis), ankylosing spondylitis, asthma, atopic dermatitis, acne, skin burns, rosacea, seborrheic dermatitis, skin ulcers, chronic obstructive pulmonary disease, contact dermatitis, cystitis, gouty arthritis, inflammatory bowel disease (such as Crohn's disease and ulcerative colitis), multiple sclerosis, osteoarthritis, pancreatitis, prostatitis, psoriasis, psoriatic arthritis, rheumatoid arthritis, tendinitis, bursitis, Sjogren's syndrome, systemic lupus erythematosus, uveitis, urticaria, vasculitis, diabetic vascular complications, migraine, atherosclerosis and associated cardiovascular disorders. Conditions that may be mentioned include atopic dermatitis, endometriosis, migraine, asthma, chronic obstructive pulmonary disease, Crohn's disease, multiple sclerosis, psoriasis, rheumatoid arthritis, systemic lupus erythematosus, ulcerative colitis and, more particularly, atherosclerosis and associated cardiovascular disorders. Other conditions that may be mentioned include metabolic syndrome, obesity, diabetes mellitus and/or diabetic vascular complications.

The term "atherosclerosis" will be understood by those skilled in the art to include any disease characterised by cholesterol accumulation, foam cell formation, inflammation and cell proliferation in a blood vessel, especially an artery wall. Cardiovascular disorders "associated with" atherosclerosis include aortic aneurysms (including abdominal and/or atherosclerotic aortic aneurysms), arteriosclerosis, peripheral arterial occlusive disease, coronary artery diseases (e.g. angina pectoris, myocardial infarction, heart attack, etc), coronary disease (including cardiac disease and heart disease, such as ischaemic heart disease), and may also include plaque or atheroma rupture and/or instability, vascular or arterial disease, ischaemic disease/ischaemia and stroke (including cerebro-vascular accident and transient ischaemic attack).

Patient groups that may be mentioned include those with acute coronary syndromes. The term "acute coronary syndrome(s)" will be understood by the skilled person to include any abnormal myocardial ischaemic state, often but not exclusively associated with chest pain and/or an abnormal electrocardiogram (ECG). Such syndromes are the most common presentation of myocardial infarction (heart attack). The skilled person will appreciate that the term is largely synonymous with the term "unstable angina", as opposed to "stable angina" (i.e. angina that develops during exertion and resolves at rest). Exertional angina that occurs at worsening rate ("crescendo angina") will similarly be regarded by the skilled person as within the definition "unstable".

According to a further aspect of the invention there is provided a method of treatment of an inflammatory disorder, and in particular atherosclerosis and/or an associated cardiovascular disorder, such as an aortic aneurysm, which method comprises the administration of a compound of the invention to a patient in need of such treatment.

Other inflammatory conditions that may be mentioned include systemic low-grade inflammation (SLGI), which will be understood to include those conditions also referred to in the literature variously as "low-grade systemic inflammation", "subclinical systemic inflammation", "chronic low-grade inflammation", "persistent low-grade inflammation" or, depending upon the context, just "low-grade inflammation" or "systemic inflammation" (see, for example März et al, *Circulation*, 110 (2004) and Nicklas et al, *CMAJ*, 172, 1199 (2005)). Although other inflammatory markers (e.g. circulating cytokines, adhesion molecules and white blood cells) are known to be indicative of SLGI and may be measured, and reduced, in accordance with the invention, SLGI is always characterised by inter alia plasma C-reactive protein (CRP) levels (in for example otherwise outwardly healthy and/or non-allergic/non-asthmatic mammalian subjects) which are less than about 10 mg/L, but which levels are above about 7 mg/L, for example above about 5 mg/L, preferably above about 3 mg/L, more preferably above about 2 mg/L, particularly above about 1 mg/L and more particularly above about 0.9 mg/L. Such plasma CRP levels may be reduced by administration of an appropriate pharmacologically-effective amount of a compound of the invention. Thus, there is further provided a compound of the invention for the reduction of plasma CRP levels in a patient (to below any one of the values mentioned hereinbefore), as well as a method of reduction of plasma CRP levels in a patient (to below any one of the values mentioned hereinbefore), which comprises administering a compound of the invention to a patient.

SLGI is known to be linked to, for example, metabolic syndrome, diabetes mellitus (e.g. type 2 diabetes), insulin resistance syndrome, obesity, cardiovascular diseases (e.g. atherosclerosis, abdominal aortic aneurysms and other cardiovascular events), and some cancers (e.g. colon cancer). Minor elevation in CRP levels may also be the only sign of disease in otherwise apparently healthy subjects.

Minor elevations in CRP can also predict undesired outcomes or complications in various medical conditions, or likelihood of dying in different diseases. In particular elevations in CRP may predict cardiovascular morbidity and mortality, and/or the development of type 2 diabetes mellitus, the risk of both of which may, in accordance with the invention, be reduced by using a compound of the invention.

Thus, there is provided a method of reducing the risk of (i.e. preventing) cardiovascular morbidity and mortality, and/or of reducing (i.e. preventing) the development of type 2 diabetes mellitus, in a patient, which method comprises:
(a) measuring a plasma CRP level in that patient;
(b) determining whether the level of plasma CRP is above one of the values mentioned hereinbefore, and particularly above about 0.9 mg/L; and
(c) if so, administering a compound of the invention to that patient for a time and at an appropriate dosage to reduce the CRP level, for example to below the relevant value mentioned hereinbefore.

The American Heart Association (AHA) and the Centers for Disease Control and Prevention (CDC) have evaluated CRP as a risk assessment tool and suggested that cut points of below 1 mg/L, between 1 and 3 mg/L, and greater than 3 mg/L be used to identify subjects at lower, average and high relative risk, of developing cardiovascular morbidity or mortality, respectively. Plasma CRP above 0.9 mg/L has also been used as a cut point for increased risk for cardiovascular events (Ridker et al, *N. Engl. J. Med.*, 352, 20 (2005)).

The term "morbidity" will be understood by the skilled person to include any diseased state, disability, illness and/or poor health generally. "Cardiovascular" morbidity therefore includes such states exhibited as a consequence of an underlying cardiovascular complication, which may in itself be a consequence of one or more of the other conditions mentioned hereinbefore, such as obesity, metabolic syndrome, (e.g. type 2) diabetes mellitus, etc (vide infra).

Type 2 diabetes mellitus is a disorder that is characterized by a decreased response of peripheral tissues to insulin (insulin resistance) and beta-cell dysfunction that is manifested as inadequate insulin secretion in the face of insulin resistance and hyperglycemia (see e.g. Robbins and Cotran, *Pathologic Basis of Disease*, $8^{th}$ edition, Saunders Elsevier). Symptoms of type 2 diabetes mellitus include chronic fatigue, excessive urine production, excessive thirst and increased fluid intake. The current World Health Organisation diagnostic criteria for diabetes are (a) a fasting plasma glucose level of at least 7.0 mmol/L or (b) a plasma glucose level of at least 11.1 mmol/L in an oral glucose tolerance test (OGTT). By "reducing the development of type 2 diabetes mellitus", we include prevention of the onset of type 2 diabetes mellitus in addition to treatment of SLGI to prevent development (e.g. worsening) of a pre-existing condition.

We have found that pemirolast does not concomitantly reduce plasma tryptase levels in the subjects with CRP above 0.9 mg/L, and also that there is no correlation between plasma levels of CRP and mast cell tryptase levels in the subjects.

Thus, it is preferred that the uses and methods related specifically to SLGI described herein are in, or of, non-allergic patients. By "non-allergic", we mean that the patient does not exhibit outward signs (at the time of receiving such a treatment) of an atopic disorder of the immune system. In this respect, such a patient may show no signs of hypersensitivity to allergens, characterised by a immunological response which includes activation of mast cells and/or basophils via IgE. Determination of whether a patient is non-allergic may be carried out routinely by for example testing (e.g. the skin) for responses to known allergens or analyzing the blood for the presence and levels of allergen-specific IgE.

It is further preferred that the uses and methods related specifically to SLGI described herein are in, or of, non-asthmatic patients. By "non-asthmatic", we mean that the patient does not exhibit outward signs (at the time of receiving such a treatment) of predisposition to chronic inflammation of the lungs in which the bronchi are reversibly narrowed by way of constriction of smooth muscle cells therein, airway inflammation and difficulties in breathing. Asthma may be allergic or non-allergic.

Preferred uses and methods of treatment of SLGI include those in which the patient is a smoker or is an ex-smoker, the subject has diabetes mellitus and/or metabolic syndrome, or has a body mass index above 25.

Other inflammatory conditions that may be mentioned include congestive heart failure, atrial fibrillation, hypertension (including essential, pulmonary arterial and/or portal hypertension); consequences of irradiation, surgery and/or trauma (including inflammation, fibrosis, scarring, and adhesions); fibrosis, scarring, and/or adhesions caused by inflammation; cancer, osteoporosis, sarcoidosis, irritable bowel syndrome, retinopathies (including diabetic retinopathy), age-related macular degeneration, nephropathies (including diabetic nephropathy), glomerulonephritis (including IgA nephritis/nephropathy).

For the avoidance of doubt, in the context of the present invention, the terms "treatment", "therapy" and "therapy method" include the therapeutic, or palliative, treatment of patients in need of, as well as the prophylactic treatment and/or diagnosis of patients which are susceptible to, inflammatory disorders, such as atherosclerosis and associated cardiovascular disorders.

"Patients" include mammalian (including human) patients.

Compounds of the invention are preferably administered locally or systemically, for example orally, intravenously or intraarterially (including by intravascular or other perivascular devices/dosage forms (e.g. stents)), intramuscularly, cutaneously, subcutaneously, transmucosally (e.g. sublingually or buccally), rectally, transdermally, nasally, pulmonarily (e.g. tracheally or bronchially), topically, or by any other parenteral route, in the form of a pharmaceutical preparation comprising the compound in a pharmaceutically acceptable dosage form. Preferred modes of delivery include oral (particularly), intravenous, cutaneous or subcutaneous, nasal, intramuscular, or intraperitoneal delivery.

Compounds of the invention will generally be administered in the form of one or more pharmaceutical formulations in admixture with a pharmaceutically acceptable adjuvant, diluent or carrier, which may be selected with due regard to the intended route of administration and standard pharmaceutical practice. Such pharmaceutically acceptable carriers are preferably sterile, pure, non-pyrogenic and are chemically inert to the active compounds and may have no detrimental side effects or toxicity under the conditions of use. Such pharmaceutically acceptable carriers may also impart an immediate, or a modified, release of a compound of the invention.

The compounds of the invention may be further processed before being admixed with a suitable carrier, diluent or adjuvant. For example, the crystalline form may be milled or ground into smaller particles.

Suitable pharmaceutical formulations may be commercially available or otherwise are described in the literature, for example, Remington *The Science and Practice of Pharmacy*, 19th ed., Mack Printing Company, Easton, Pa. (1995) and *Martindale—The Complete Drug Reference* (35$^{th}$ Edition) and the documents referred to therein, the relevant disclosures in all of which documents are hereby incorporated by reference. Otherwise, the preparation of suitable formulations may be achieved non-inventively by the skilled person using routine techniques.

The amount of compound of the invention in the formulation will depend on the severity of the condition, and on the patient, to be treated, as well as the compound(s) which is/are employed, but may be determined non-inventively by the skilled person.

Depending on the disorder, and the patient, to be treated, as well as the route of administration, compounds of the invention may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

Administration of compounds of the invention may be continuous or intermittent (e.g. by bolus injection). The dosage may also be determined by the timing and frequency of administration.

Suitable doses include those referred to in the medical literature, such as *Martindale—The Complete Drug Reference* (35$^{th}$ Edition) and the documents referred to therein, the relevant disclosures in all of which documents are hereby incorporated by reference. Suitable doses of compounds of the invention (calculated as the free acid) are therefore in the range of about 0.01 mg/kg of body weight to about 1,000 mg/kg of body weight. More preferred ranges are about 0.1 mg/kg to about 20 mg/kg on a daily basis, when given orally.

However, suitable doses of pemirolast are known to those skilled in the art. For example, peroral doses (calculated as the free acid) may be in the range of about 0.1 mg to about 1.2 g, such as about 0.5 mg to about 900 mg, per day. For example suitable lower limits of daily dose ranges are about 1 mg, such as about 2 mg, for example about 5 mg, such as about 10 mg, and more preferably about 20 mg; and suitable upper limits of daily dose ranges are about 200 mg, for example about 100 mg, such as about 80 mg, and more preferably about 60 mg. Daily peroral doses may thus be between about 2 mg and about 60 (e.g. about 50) mg, such as about 5 mg and about 45 (e.g. about 40) mg, and preferably about 10 mg and about 35 (e.g. about 30) mg. Suitable individual doses may be between about 10 mg and about 100 mg, such as between about 20 mg and about 90 mg, e.g. between about 30 mg and about 80 mg, per day. Preferred doses are in the range of about 40 mg to about 80 mg, and particularly about 60 mg daily. The skilled person will appreciate that doses may be on a once daily basis, or may be divided into (e.g. equal) twice, or three times, daily doses (preferably twice).

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may also be combined with one or more active ingredients that are useful in the treatment of inflammatory disorders as defined herein.

According to a further aspect of the invention therefore, there is also provided a combination product comprising:

(a) a compound of the invention; and
(b) one or more active ingredient that is useful in the treatment of an inflammatory disorder, or a pharmaceutically-acceptable salt or solvate thereof.

Such combination products provide for the administration of a compound of the invention in conjunction with an active ingredient that is useful in the treatment of an inflammatory disorder, and may thus be presented either as separate formulations, wherein at least one of those formulations comprises a compound of the invention, and at least one comprises the other active ingredient, or may be presented (i.e. formulated) as a combined preparation (i.e. presented as a single formulation including a compound of the invention and another active ingredient).

Thus, there is further provided:
(1) a pharmaceutical formulation including a compound of the invention; an active ingredient that is useful in the treatment of an inflammatory disorder, or a pharmaceutically-acceptable salt or solvate thereof; and a pharmaceutically-acceptable adjuvant, diluent or carrier (which formulation is hereinafter referred to as a "combined preparation"); and
(2) a kit of parts comprising components:
    (A) a pharmaceutical formulation including a compound of the invention, in admixture with a pharmaceutically-acceptable adjuvant, diluent or carrier; and
    (B) a pharmaceutical formulation including an active ingredient that is useful in the treatment of an inflammatory disorder, or a pharmaceutically-acceptable salt or solvate thereof, in admixture with a pharmaceutically-acceptable adjuvant, diluent or carrier,
which components (A) and (B) are each provided in a form that is suitable for administration in conjunction with the other.

According to a further aspect of the invention, there is provided a method of making a kit of parts as defined above, which method comprises bringing component (A), as defined above, into association with a component (B), as defined above, thus rendering the two components suitable for administration in conjunction with each other.

By bringing the two components "into association with" each other, we include that components (A) and (B) of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Thus, there is further provided a kit of parts comprising:
(I) one of components (A) and (B) as defined herein; together with
(II) instructions to use that component in conjunction with the other of the two components.

The kits of parts described herein may comprise more than one formulation including an appropriate quantity/dose of compound of the invention, and/or more than one formulation including an appropriate quantity/dose of the other active ingredient/salt/solvate, in order to provide for repeat dosing. If more than one formulation (comprising either active compound) is present, such formulations may be the same, or may be different in terms of the dose of either compound, chemical composition(s) and/or physical form(s).

With respect to the kits of parts as described herein, by "administration in conjunction with", we include that respective formulations comprising compound of the invention and other active ingredient (or salt/solvate thereof) are administered, sequentially, separately and/or simultaneously, over the course of treatment of the relevant condition.

Thus, in respect of the combination product according to the invention, the term "administration in conjunction with" includes that the two components of the combination product (compound of the invention and other active ingredient) are administered (optionally repeatedly), either together, or sufficiently closely in time, to enable a beneficial effect for the patient, that is greater, over the course of the treatment of the relevant condition, than if either a formulation comprising the compound of the invention, or a formulation comprising the other active ingredient, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

Further, in the context of a kit of parts according to the invention, the term "in conjunction with" includes that one or other of the two formulations may be administered (optionally repeatedly) prior to, after, and/or at the same time as, administration of the other component. When used in this context, the terms "administered simultaneously" and "administered at the same time as" include that individual doses of compound of the invention and other active ingredient are administered within 48 hours (e.g. 24 hours) of each other.

Active ingredients that are useful in the treatment of inflammatory disorders as defined herein include thromboxane A2 antagonists, P2Y$_{12}$ antagonists, PPAR$_\gamma$ agonists, compounds that inhibit the formation and/or action of angiotensin II, other platelet aggregation inhibiting drugs and, more preferably, statins.

The term "thromboxane A2 antagonist" includes any compound that is capable of inhibiting, to an experimentally-determinable degree in in vitro and/or in vivo tests, the effects of thromboxane A2 by one or more of (i) blocking the thromboxane TP receptor, (ii) inhibiting the enzyme thromboxane synthase, or (iii) inhibiting (e.g. selectively) platelet cyclooxygenase-1, thereby inhibiting e.g. platelet aggregation.

Preferred thromboxane A2 antagonists include aspirin/acetylsalicylic acid, more preferably egualen, particularly ozagrel, more particularly, picotamide and terutroban, especially seratrodast and more especially ramatroban.

The term "P2Y$_{12}$ antagonist" includes any compound that is capable of inhibiting (e.g. selectively), to an experimentally-determinable degree in in vitro and/or in vivo tests, the binding of ADP to the platelet receptor P2Y$_{12}$, thereby inhibiting platelet aggregation.

Preferred P2Y$_{12}$ antagonists include prasugrel, ticagrelor and, particularly, clopidogrel.

The term "PPAR$_\gamma$" agonist includes any compound that is capable of binding to, and/or influencing the function of, the peroxisome proliferator-activated gamma receptor to an experimentally-determinable degree in in vitro and/or in vivo tests.

Preferred PPAR$_\gamma$ agonists therefore include the compounds collectively known together as thiazolidinediones, including rivoglitazone, naveglitazar, balaglitazone or, more preferably, rosiglitazone and, especially, pioglitazone. Other PPAR$_\gamma$ agonists that may be mentioned include chiglitazar, etalocib, farglitazar, lobeglitazone, netoglitazone, sodelglitazar, as well as those defined in the literature by way of following developmental drug codes: THR-0921 (Theracos Inc.) or, more preferably, AVE-0847 and AVE-0897 (both Sanofi-Aventis), CLX-0921 (Calyx Therapeutics), CS-7017 (Daiichi Sankyo Co Ltd), DRF-11605 (Dr Reddy's Laboratories Ltd), GFT-505 (Genfit SA), GSK-376501 (GlaxoSmithKline plc), INT-131 (Amgen Inc; InteKrin Therapeutics), (LBM-642; cevoglitazar; Novartis AG), ONO-5129 (Ono Pharmaceutical Co Ltd), (PLX-204; indeglitazar; Plexxikon Inc) and SDX-101.

The term "compound that inhibits the formation and/or action of angiotensin II" includes any compound that is capable of inhibiting (e.g. selectively), to an experimentally-determinable degree in in vitro and/or in vivo tests, the formation and/or action of angiotensin II and will be understood to include angiotensin converting enzyme (ACE) inhibitors, angiotensin receptor blockers (ARBs) and renin inhibitors.

The term "angiotensin converting enzyme (ACE) inhibitor" includes any compound that is capable of inhibiting (e.g. selectively), to an experimentally-determinable degree in in vitro and/or in vivo tests, the conversion of angiotensin I to angiotensin II.

ACE inhibitors that may be mentioned include alacepril, benazepril, captopril, ceronapril, cilazapril, delapril, enalapril, fosinopril, gemopatrilat, glycopril, idrapril, ilepatril, imidapril, libenzapril, lisinopril, microginin-FR1, mixanpril, moexipril, moexiprilat, moveltipril, omapatrilat, Prentyl, perindopril, quinapril, ramipril, sampatrilat, spirapril, Synecor, temocapril, trandolapril, utibapril, zofenopril and zabiciprilat. More preferred ACE inhibitors include benazepril, cilazapril, ilepatril, imidapril, moexipril, spirapril, temocapril and zofenopril, more preferably fosinopril and trandolapril, more particularly enalapril, lisinopril and quinapril, and especially captopril, perindopril and ramipril.

The term "angiotensin receptor blocker (ARB)" will be understood by the skilled person to be largely synonymous with the term "angiotensin II AT1 receptor antagonist", and thus includes any substance that is capable of blocking the activation (e.g. selectively), to an experimentally-determinable degree in in vitro and/or in vivo tests, of the angiotensin II AT1 receptor.

ARBs that may be mentioned include azilsartan, azilsartan medoxomil, candesartan, candesartan cilexetil, the angiokine Dival, elisartan, elisartan potassium, eprosartan, embusartan, fimasartan, fonsartan, irbesartan, losartan, milfasartan, olmesartan, pomisartan, pratosartan, ripisartan, saprisartan, saralasin, tasosartan, telmisartan, valsartan and zolasartan. More preferred ARBs include azilsartan, eprosartan, fimasartan and pratosartan, more preferably telmisartan, more particularly irbesartan and olmesartan, and especially candesartan, losartan and valsartan.

The term "renin inhibitor" will be understood by the skilled person to includes any substance that is capable of blocking the function (e.g. selectively), to an experimentally-determinable degree in in vitro and/or in vivo tests, of renin in the renin-angiotensin system.

Renin inhibitors that may be mentioned include cyclothiazomycin, aliskiren, ciprokiren, ditekiren, enalkiren, remikiren, terlakiren and zankiren. Preferred renin inhibitors include aliskiren.

Compounds that inhibit the formation and/or action of angiotensin II also include those defined in the literature by way of the following developmental drug codes: 100240, 606A, A-65317, A-68064, A-74273, A-81282, A-81988, A-82186, AB-47, BIBR-363, BIBS-222, BIBS-39, BILA-2157BS, BL-2040, BMS-180560, BMS-181688, BMS-182657, BMS-183920, BMS-184698, BRL-36378, CGP-38560, CGP-38560a, CGP-42112-A, CGP-42112, CGP-421132-B, CGP-48369, CGP-49870, CGP-55128A, CGP-56346A, CGS-26670, CGS-26582, CGS-27025, CGS-28106, CGS-30440, CHF-1521, CI-996, CL-329167, CL-331049, CL-332877, CP-191166, CP-71362, CV-11194, CV-11974, DMP-581, DMP-811, DU-1777, DuP-167, DuP-532, E-4030, E-4177, EC-33, EK-112, EMD-56133, EMD-58265, EMD-66684, ER-32897, ER-32935, ER-32945, ES-1005, ES-305, ES-8891, EXP-408, EXP-597, EXP-6803, EXP-7711, EXP-929, EXP-970, FPL-66564, GA-0050, GA-0056, GA-0113, FK-739, FK-906, GR-137977, GR-70982, GW-660511, Hoe-720, ICI-219623, ICI-D-6888, ICI-D-8731, JT-2724, KR-30988, KRH-594, KR1-1314, KT3-866, KW-3433, L-158809, L-158978, L-159093, L-159689, L-159874, L-159894, L-159913, L-161177, L-161290, L-161816, L-162223, L-162234, L-162313, L-162389, L-162393, L-162441, L-162537, L-162620, L-163007, L-163017, L-163579, L-163958, L-363564, L-746072, LCY-018, LR-B-057, LY-285434, LY-301875, LY-315996, MDL-102353, MDL-27088, MDL-27467A, ME-3221, MK-8141, MK-996, PD-123177, PD-123319, PD-132002, PD-134672, PS-433540, RB-106, RS-66252, RU-64276, RU-65868, RWJ-38970, RWJ-46458, RWJ-47639, RXP-407, S-2864, S-5590, SB-203220, SC-50560, SC-51316, SC-51895, SC-52458, SC-54629, SC-565254, Sch-47896, Sch-54470, SK-1080, SKF-107328, SL-910102, SQ-30774, SQ-31844, SQ-33800, SR-43845, TA-606, TH-142177, U-97018, UK-63831, UK-77568, UK-79942, UP-275-22, WAY-121604, WAY-126227, VNP-489, XH-148, XR-510, YM-21095, YM-26365, YM-31472, YM-358 and ZD-7155.

Other platelet aggregation inhibiting drugs that may be mentioned include nitric oxide-donating derivatives of aspirin/acetylsalicylic acid (e.g. NCX-4016, NicOx S.A.) or, more preferably, anagrelide, argatroban, beraprost, cangrelor, cilostazol, dipyridamole, limaprost, parogrelil, procainamide, sarpogrelate (e.g. sarpogrelate hydrochloride), ticlopidine, tirofiban and triflusal, as well as those defined in the literature by way of following developmental drug codes: DA-697b (see international patent application WO 2007/032498; Daiichi Seiyaku Co Ltd), DG-041 (deCODE Genetics Inc), K-134 (CAS RN 189362-06-9), PL-2200 (CAS RN 50-78-2), PRT-60128 (Portola Pharmaceuticals Inc), SH-529 (an iloprost/beta-cyclodextrin clathrate; Bayer Schering Pharma AG) and YY-280 (a combination therapy of ticlopidine and EGb-761 (tanamin; a *Ginkgo biloba* extract; Yuyu Inc.)).

The term "statin" includes any inhibitor of HMG-CoA reductase and includes fluvastatin, simvastatin, lovastatin, rosuvastatin, pitavastatin, glenvastatin, cerivastatin, pravastatin, mevastatin, bervastatin, dalvastatin and atorvastatin.

Other statins that may be mentioned include Acitemate, benfluorex, Clestin, colestolone, dihydromevinolin, meglutol, rawsonol, as well as the compounds with the following code names: ATI-16000, BAY-10-2987, BAY-x-2678, BB-476, BIO-002, BIO-003, BIO-2, BMS-180431, CP-83101, DMP-565, FR-901512, GR-95030, HBS-107, KS-01-019, L-659699, L-669262, NR-300, P-882222, PTX-023595, RP 61969, S-2468, SC-32561, sc-45355, SDZ-265859, SQ-33600, U-20685, and NO-enhancing/releasing statins, such as NCX-6550 (nitropravastatin) and NCX-6560 (nitroatorvastatin).

More preferred statins include pitavastatin (e.g. Livalo®, Pitava®), fluvastatin (e.g. Lescol®, simvastatin (e.g. Zocor®, Lipex®), lovastatin (e.g. Mevacor®, Altocor®), rosuvastatin (e.g. Crestor®), pravastatin (e.g. Pravachol®, Selektine®, Lipostat®) and atorvastatin (e.g. Lipitor®, Torvast®). Particularly preferred statins include pitavastatin, more preferably simvastatin, more particularly atorvastatin and, especially, rosuvastatin.

Pharmaceutically-acceptable salts of other active ingredients that are useful in the treatment of inflammation that may be mentioned include acid addition salts and base addition salts. Such salts may be formed by conventional means, for example by reaction of a free acid or a free base form of an active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of an active ingredient in the form of a salt with another counter-ion, for example using a suitable ion exchange resin.

Salts of picotamide that may be mentioned include hydrochloride, bisulfate, maleate and tosylate salts. Salts of ozagrel, terutroban, egualen and aspirin that may be mentioned include alkali metal salts, such as lithium, sodium and potassium salts. Preferred salts of ozagrel and egualen include sodium salts.

Preferred salts of clopidogrel include bisulfate salts, but other salts that may be mentioned, as well as salts of ticagrelor that may be mentioned, include hydrochloride, bisulfate, maleate and tosylate salts. Preferred salts of prasugrel that may be mentioned include hydrochloride salts, but other salts that may be mentioned include bisulfate, maleate and tosylate salts.

Preferred salts of pioglitazone that may be mentioned include hydrochloride salts, but other salts that may be mentioned include bisulfate, maleate and tosylate salts. Preferred salts of rosiglitazone that may be mentioned include maleate salts, but other salts that may be mentioned include hydrochloride, bisulfate and tosylate salts. Salts of rivoglitazone that may be mentioned include hydrochloride, bisulfate, maleate and tosylate salts. Preferred salts of naveglitazar include sodium salts, but other salts that may be mentioned include lithium and potassium salts. Preferred salts of balaglitazone that may be mentioned include sodium, potassium and calcium salts.

Preferred salts of compounds that inhibit the formation and/or action of angiotensin II include, for example, hydrochloride, bisulfate, maleate, mesylate, tosylate, alkaline earth metal salts, such as calcium and magnesium, or alkali metal salts, such as sodium and potassium salts. Such salts may be prepared using routine techniques for compounds including perindopril, enalapril, lisinopril, quinapril, irbesartan, olmesartan, trandolapril, telmisartan, benazepril, cilazapril, moexipril, spirapril, eprosartan and fimasartan. Hydrochloride, bisulfate, maleate, mesylate and tosylate salts are preferred for compounds such as ramipril and aliskiren. Alkaline earth, and more particularly alkali, metal salts are preferred for compounds such as candesartan, valsartan, captopril, losartan and, particularly, fosinopril, preferred salts of which include calcium, magnesium, potassium and, particularly, sodium salts. Preferred salts of benazepril and moexipril that may be mentioned include hydrochloride salts, but other salts that may be mentioned include bisulfate, maleate, mesylate and tosylate salts. Preferred salts of eprosarten that may be mentioned include mesylate salts, but other salts that may be mentioned include hydrochloride, bisulfate, maleate and tosylate salts.

Preferred salts of statins include sodium, potassium and calcium salts, such as pitavastatin calcium, fluvastatin sodium, pravastatin sodium, rosuvastatin calcium and atorvastatin calcium.

Suitable doses of other active ingredients that are useful in the treatment of inflammation are known to those skilled in the art and include those listed for the drugs in question to in the medical literature, such as *Martindale—The Complete Drug Reference* (35$^{th}$ Edition) and the documents referred to therein, the relevant disclosures in all of which documents are hereby incorporated by reference.

Wherever the word "about" is employed herein, for example in the context of amounts (e.g. values, weights, volumes, moles), temperatures, degrees of crystallinity, degrees of degradation, degrees of purity, degrees of dissolution and doses of active ingredients, it will be appreciated that such variables are approximate and as such may vary by ±10%, for example ±5% and preferably ±2% (e.g. ±1%) from the numbers specified herein.

Compounds of the invention have the advantage that they are in a form which provides for improved ease of handling, and may be produced in forms which have improved chemical and solid state stability when compared to forms of pemirolast prepared previously. Thus, compounds may be stable when stored over prolonged periods.

Compounds of the invention also have improved solubility and hygroscopicity profiles when compared to known and/or commercially-available forms of pemirolast. Compounds of the invention may also have an improved taste profile when compared to known and/or commercially-available forms of pemirolast.

Compounds of the invention may also have the advantage that they may be prepared in good yields, in a higher purity, in less time, more conveniently, and at a lower cost, than forms of pemirolast prepared previously.

The compounds of the invention may also have the advantage that, in the treatment of the conditions mentioned hereinbefore, they may be more convenient for the physician and/or patient than, be more efficacious than, be less toxic than, have a broader range of activity than, be more potent than, produce fewer side effects than, or may have other useful pharmacological properties over, similar compounds known in the prior art for use in the treatment of inflammatory disorders (such as atherosclerosis and associated cardiovascular conditions) or otherwise.

The invention is illustrated, but in no way limited, by the following examples, with reference to the enclosed figures in which.

GENERAL PROCEDURES FOR EXAMPLES 1 TO 5

Figure 1:
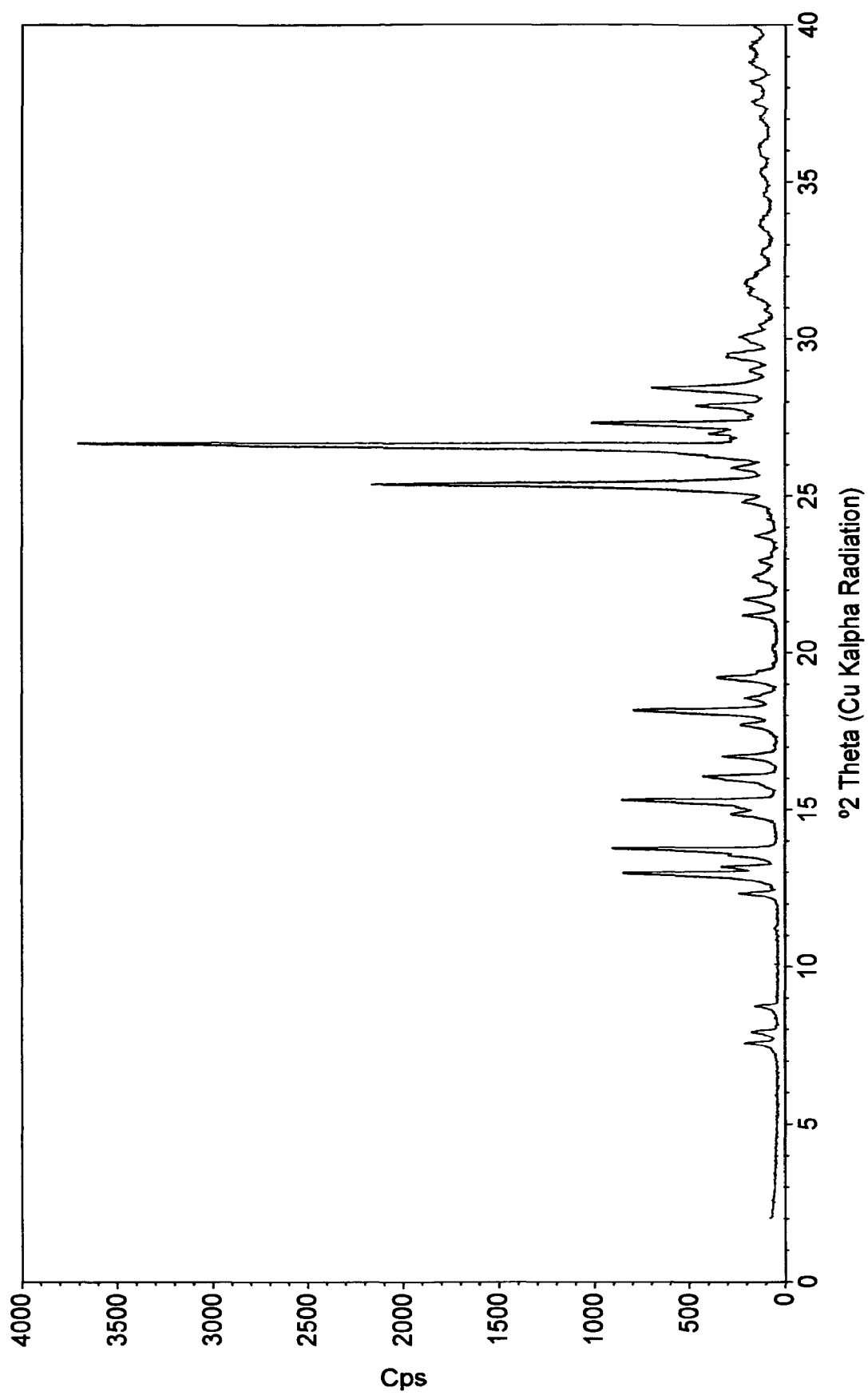
FIG. 1 shows a powder X-ray diffractogram for the crystalline form of pemirolast sodium hemihydrate obtained by way of Example 1.

FT-Raman spectra were recorded on a Bruker RFS 100 FT-Raman system with a near infrared Nd:YAG laser operating at 1064 nm and a liquid nitrogen-cooled germanium detector. 64 scans with a resolution of 2 cm$^{-1}$ were accumulated in the range from 3500 to 50 cm$^{-1}$. In general, 100 mW laser power was used.

Powder X-ray diffraction was carried out using a Bruker D8; Copper Kα radiation, 40 kV/40 mA; LynxEye detector, 0.02 °2θ step size, 37 s step time. Sample preparation: The samples were generally measured without any special treatment other than the application of slight pressure to get a flat surface. Silicon single crystal sample holder types: a) standard holder 0.1 mm deep, b) 0.5 mm deep, 12 mm cavity diameter, c) 1.0 mm deep, 12 mm cavity diameter. All samples measured on the Bruker D8 were rotated during the measurement. Unless otherwise specified, an ambient air atmosphere was used. Selected samples were measured on a Philips X'pert PW 3040 or Philips PW1710 with Copper Kα radiation, 0.02 °2θ step size, 2 s step-1, 2-50 °2θ; the samples were measured without any special treatment other than the application of slight pressure to get a flat surface. Unless otherwise specified, an ambient air atmosphere was used. (Forms prepared in accordance with the Examples below showed "essentially" the same PXRD diffraction patterns as other Examples disclosed below, when it was clear from the relevant patterns (allowing for experimental error) that the same crystalline form had been formed. Thus, limits of experimental error for PXRD distance values may be in the range ±2 or thereabouts on the last decimal place as employed in any part of this specification.)

Elemental analysis for C, H and N was performed by combustion using either a Leco CHN 800 or Leco CHNS 932 instrument. Elemental analysis of O was performed by pyrolysis using a Leco RO-478 instrument. Elemental analysis of Na was performed by atom absorption spectrometry.

$^1$H/$^{13}$C NMR spectra were recorded at a Bruker DPX300 instrument. Otherwise, $^1$H NMR spectra were recorded on a Varian MERCURY+400 spectrometer (400 MHz). Spectra were recorded at ambient temperature and the chemical shifts are reported as δ values (ppm) referenced to TMS via the solvent signals δ 7.26 ppm CHCl$_3$, δ 2.50 ppm DMSO and δ 4.79 ppm H$_2$O.

Analytical mass spectra were recorded on a LC-MS system using a Gilson HPLC system with a Finnigan ThermoQuest AQA quadrupole mass spectrometer equipped with an Onyx Monolithic C18, 50 mm×4.6 mm column (Phenomenex), a flow rate of 4 mL/min with a gradient acetonitrile/water and 0.05% formic acid, or a GC-MS instrument equipped with a Varian chrompack Capillary column CP-SIL 8 CB Low Bleed/MS (30 m_0.22 mm, 0.25 mm) and utilizing an ion generation potential of 70 eV.

Differential Scanning calorimetry was recorded on a Perkin Elmer DSC 7. Closed gold crucibles, heating rate: 10 K/min, range: 50° C. to 350° C. Temperatures related to thermal events recorded in the course of the DSC analysis are peak temperatures (min/max) of the respective thermal event.

TG-FTIR was recorded on a Netzsch Thermo-Microbalance TG 209 with Bruker FT-IR Spectrometer Vector 22. Al-crucible (open or with micro hole), N2 atmosphere, heating rate 10 K/min, range 25-250° C.

HPLC was performed on a TSP HPLC (UV3000, AS3000, P4000, SCM1000 Soft. Version 4.1); column: Waters, X Terra MS C18 4.6×100 mm, 5µ (CC01); mobile phase A: H$_2$O+ 0.1% TFA; mobile phase B: acetonitrile+0.1% TFA; reference concentration: ca. 0.09 mg/mL; retention time: 6.6 minutes; gradient: 0.0 min: A:95%/B:5%; 20.0 min: A:5%/B: 95%; 21.0 min: A:95%/B:5%; 30.0 min: A:95%/B:5%; flow: 1.0 mL/minute; injection volume: 10 µL; wavelength: 254 nm. Dynamic Vapor Sorption (DVS) measurements were carried out on a Sorption Measurement System SPS11-100n. The sample was placed in an aluminum crucible and the sample was allowed to equilibrate at a given RH before starting a pre-defined humidity program. (1) 2 h at 50% RH; (2) 50→0% RH (5%/h); (3) 5 h at 0% RH; (4) 0→95% RH (5%/h); (5) 5 h at 95% RH; (6) 95→50% RH (5%/h); (7) 2 h at 50% RH. Hygroscopicity was classified according to the European Pharmacopoeia (storage at 80% RH/25° C. for 24 hours). The mass change at 85% RH was used for classification, as compared to the starting material (at ambient conditions)—very hygroscopic: increase of mass ≥15%; hygroscopic: increase of mass is less than 15% and equal to or greater than 2%; slightly hygroscopic: increase of mass is less than 2% and equal to or greater than 0.2%; deliquescent: sufficient water is absorbed to form a liquid.

EXAMPLE 1

Pemirolast Sodium Hemihydrate

Pemirolast free acid was prepared by dissolving pemirolast potassium in water and acidifying to pH 1 with 6M HCl which caused the free acid to precipitate from solution. The crystals formed were filtered, washed with water and dried under vacuum. Pemirolast potassium was in turn prepared analogously to the methodology described in Example 4 (steps Ia and Ib) below, using 2M KOH instead of 2M NaOH, and recrystallising from water:isopropanol in a 1:2, instead of a 2:1, ratio.

Pemirolast free acid (89 mg) was suspended in 783 µL of 0.5 M sodium methoxide in methanol (Fluka). The suspension was stirred for one day. A precipitate was formed. After filtration and drying under vacuum for about 2 hours, a solid material was obtained (yield: 81 mg).

An elemental composition analysis is summarized in Table 1 below. The data indicate a hemihydrate of a pemirolast sodium salt with a 1:1 stoichiometry. The theoretical data were calculated for the formula: Na(C$_{10}$H$_7$N$_6$O)×0.5 H$_2$O.

TABLE 1

| Element | Theoretical content (% m/m) | Measured content (% m/m) |
| --- | --- | --- |
| C | 46.34 | 46.64 ± 0.3 |
| H | 3.11 | 3.24 ± 0.3 |
| N | 32.42 | 32.62 ± 0.3 |
| O | 9.25 | 9.45 ± 0.3 |
| Na | 8.87 | 8.37 |

The PXRD pattern of the form obtained by way of Example 1 is shown in FIG. 1 and is tabulated in Table 2 below.

TABLE 2

| Angle (2-Theta °) | d value (Angstrom) | Intensity (Cps) | Relative Intensity (%) |
|---|---|---|---|
| 7.48 | 11.8 | 124.0 | 4.6 |
| 7.83 | 11.3 | 97.1 | 3.6 |
| 8.65 | 10.2 | 86.2 | 3.2 |
| 12.28 | 7.2 | 147.0 | 5.4 |
| 12.89 | 6.9 | 562.0 | 20.7 |
| 13.15 | 6.7 | 208.0 | 7.7 |
| 13.67 | 6.5 | 623.0 | 22.9 |
| 14.83 | 5.97 | 180.0 | 6.6 |
| 15.23 | 5.81 | 569.0 | 20.9 |
| 15.99 | 5.54 | 262.0 | 9.7 |
| 16.67 | 5.32 | 212.0 | 7.8 |
| 17.66 | 5.02 | 149.0 | 5.5 |
| 18.09 | 4.90 | 543.0 | 20.0 |
| 18.50 | 4.79 | 127.0 | 4.7 |
| 19.13 | 4.64 | 226.0 | 8.3 |
| 21.10 | 4.21 | 138.0 | 5.1 |
| 21.62 | 4.11 | 133.0 | 4.9 |
| 22.32 | 3.98 | 102.0 | 3.7 |
| 22.83 | 3.89 | 73.9 | 2.7 |
| 23.63 | 3.76 | 101.0 | 3.7 |
| 24.74 | 3.60 | 150.0 | 5.5 |
| 25.21 | 3.53 | 1686.0 | 62.0 |
| 25.82 | 3.45 | 174.0 | 6.4 |
| 26.45 | 3.37 | 2718.0 | 100.0 |
| 26.91 | 3.31 | 272.0 | 10.0 |
| 27.21 | 3.28 | 729.0 | 26.8 |
| 27.81 | 3.21 | 326.0 | 12.0 |
| 28.34 | 3.15 | 486.0 | 17.9 |
| 28.92 | 3.08 | 114.0 | 4.2 |
| 29.40 | 3.04 | 182.0 | 6.7 |
| 30.00 | 2.98 | 151.0 | 5.6 |
| 30.37 | 2.94 | 70.5 | 2.6 |
| 30.87 | 2.89 | 56.6 | 2.1 |
| 31.37 | 2.85 | 113.0 | 4.2 |
| 31.70 | 2.82 | 122.0 | 4.5 |
| 32.03 | 2.79 | 78.7 | 2.9 |
| 32.65 | 2.74 | 72.4 | 2.7 |
| 33.58 | 2.67 | 73.5 | 2.7 |
| 34.49 | 2.60 | 56.8 | 2.1 |
| 35.20 | 2.55 | 65.6 | 2.4 |
| 35.89 | 2.50 | 65.5 | 2.4 |
| 36.06 | 2.49 | 67.1 | 2.5 |
| 36.96 | 2.43 | 58.2 | 2.1 |
| 37.45 | 2.40 | 93.0 | 3.4 |
| 38.10 | 2.36 | 102.0 | 3.8 |
| 38.73 | 2.32 | 94.9 | 3.5 |
| 39.24 | 2.29 | 107.0 | 3.9 |
| 39.92 | 2.26 | 90.3 | 3.3 |

The salt was highly crystalline.

Figure 2:
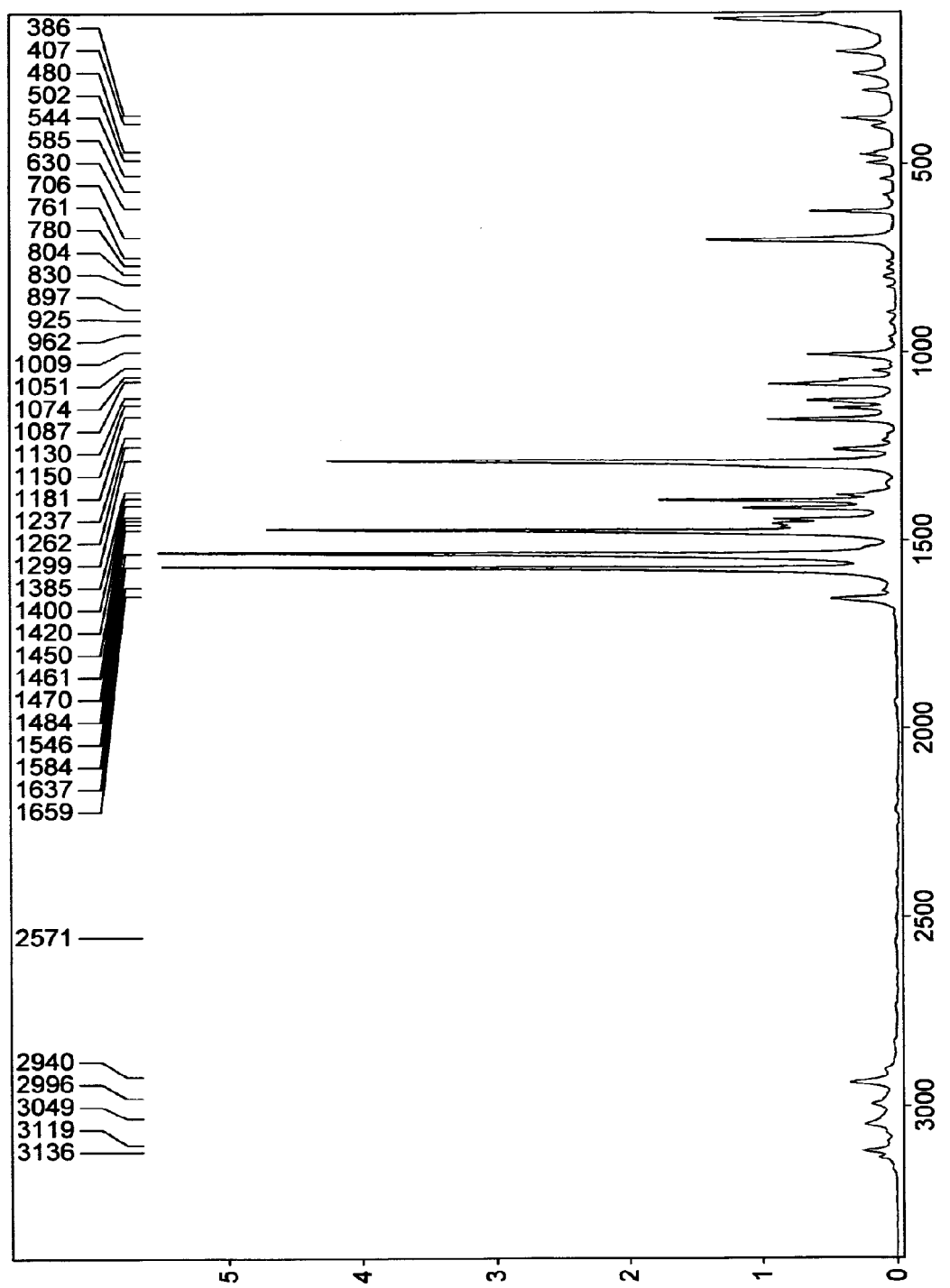
FIG. 2 shows an FT-Raman spectra for the crystalline form of pemirolast sodium hemihydrate obtained by way of Example 1.

The FT-Raman spectrum of the form obtained by way of Example 1 is shown in FIG. 2.

NMR, DSC, TG-FTIR and DVS analyses were also carried out. DSC showed one endotherm, at 280.3° C. DVS analysis reveals that the title compound is hygroscopic according to the above classification system (significant water uptake starts above 80% RH). (By contrast, DVS analysis reveals that pemirolast potassium is very hygroscopic according to the above classification system (significant water uptake starts above 70% RH).)

EXAMPLE 2

Pemirolast Sodium Hemihydrate

Pemirolast free acid (prepared as described in Example 1 above; 90 mg) was suspended in 791 μL of 0.5 M sodium methoxide in methanol (Fluka). The suspension was stirred for one day. A precipitate was formed. After filtration and drying under vacuum for about 1.5 hours, a solid material was obtained (yield: 59 mg).

The crystals were analyzed by FT-Raman. The relevant spectrum was essentially the same as that exhibited by the form obtained according to Example 1 above.

EXAMPLE 3

Comparison of Solubilities

About 40 mg of a sample (obtained by way of the procedure described in Example 2 above) was dispersed in 0.25 mL of doubly distilled water. The suspension was shaken at 22° C. for 24 hours. Afterwards, a fast solid/liquid-separation was performed using an Eppendorf Thermomixer Comfort (400 rpm). The suspensions were filtered with Millipore Centrifugal Filter Devices (PTFE filter; 0.2 μm) in a Centrifuge Hettich EBA 12 R (15,000 g, 1 minute, 22° C.). The concentration of the sample in the filtrate was analyzed by HPLC, and the solid phase was analyzed by FT-Raman spectroscopy.

The compound of Example 2 exhibited an aqueous solubility of 23.64 mg/mL under the studied conditions. The saturated solution had a pH of 8.0.

The aqueous solubility of the potassium salt of pemirolast (prepared as described in Example 1, second paragraph, and Example 2, above, using 3.4 M potassium methoxide in methanol (Fluka) instead of 0.5 M sodium methoxide in methanol) was determined in a similar fashion and was found to be 192.38 mg/mL under the studied conditions. The saturated solution had a pH of 9.0. (The aqueous solubility of commercially-available pemirolast potassium is reported to be 179-182 mg/mL; source: the Pharmaceutical Interview Form supra.)

COMPARATIVE EXAMPLE 4

Synthesis of Pemirolast Sodium

The sodium salt of pemirolast was prepared by way of the following two methods:

(I)

(Ia) 9-Methyl-3-(1H-tetrazol-5-yl)-4H-pyrido[1,2-a]pyrimidin-4-one (Pemirolast)

This was synthesized according to the method described by Sano and Ishihara (*Heterocycles*, 48, 775 (1998)) starting from malononitrile (1.64 g, 24.8 mmol; Acros Organics), 2-amino-3-picoline (2.51 mL, 24.8 mmol; Acros Organics), ethyl orthoformate (4.55 mL, 27.3 mmol; Sigma-Aldrich) and sodium azide (1.78 g, 27.4 mmol; Sigma-Aldrich) to give subtitle compound (2.64 g; 46.7%).

$^1$H NMR (DMSO-d6) δ: 9.21 (s, 1H, CH), 9.16-9.11 (m, 1H, CH), 8.13-8.07 (m, 1H, CH), 7.58-7.51 (m, 1H, CH), 2.62 (s, 3H, CH$_3$).

(Ib) 9-Methyl-3-(1H-tetrazol-5-yl)-4H-pyrido[1,2-a]pyrimidin-4-one (Pemirolast), Sodium Salt 9-Methyl-3-(1H-tetrazol-5-yl)-4H-pyrido[1,2-a]pyrimidin-4-one (2 g, 8.76 mmol; from step Ia above) was suspended in 2-propanol (9 mL) and 2M NaOH (8.8 mL, 17.6 mmol) was added. The reaction mixture was heated to 50° C. for 1 hour. Crude title compound precipitated after treatment with another 17 mL of 2-propanol. The solid material was collected by filtration after cooling in an ice bath and re-dissolved in 100 mL water. Undissolved material was removed by filtration and the filtrate was evaporated. The residue was recrystallised from water and 2-propanol in a 2:1 ratio and dried in vacuum to give the pure Na salt of pemirolast (1.26 g, 57.5%).

$^1$H NMR (D$_2$O) δ: 8.86-8.80 (m, 1H, CH), 8.57 (s, 1H, CH), 7.68-7.59 (m, 1H, CH), 7.22-7.13 (m, 1H, CH), 2.39 (s, 3H, CH$_3$).

(II) (Methodology described in U.S. Pat. No. 4,122,274.)

(IIa) Ethyl 2-cyano-3-(3-methyl-2-pyridylamino)acrylate

A solution of ethyl ethoxymethylenecyanoacetate (7.82 g, 46.2 mmol; Sigma-Aldrich) and 2-amino-3-picoline (4.67 mL, 46.2 mmol; Acros Organics) in toluene (4 mL) was heated at 100° C. for 15 minutes. The reaction mixture was cooled and the subtitle product (10.45 g, 97.8%) was collected by filtration.

GC-MS (70 eV) m/z (relative intensity) 231 (M$^+$, 15), 158 (100)

$^1$H NMR (CDCl$_3$) δ: 11.20-11.07 (m, 1H, NH), 8.82 (d, J=12.4 Hz, 1H, CH), 8.22-8.17 (m, 1H, CH), 7.53-7.47 (m, 1H, CH), 7.07-6.96 (m, 1H, CH), 4.31 (q, J=7.2 Hz, 2H, CH$_2$), 2.33 (s, 3H, CH$_3$), 1.37 (t, J=7.2 Hz, 3H, CH$_3$).

(IIb) 9-Methyl-3-(1H-tetrazol-5-yl)-4H-pyrido[1,2-a]pyrimidin-4-one (Pemirolast)

THF (375 mL) was cooled to −30° C. and aluminium chloride (7.30 g, 54.7 mmol) was added followed by NaN$_3$ (10.65 g, 163.8 mmol). The reaction mixture was heated under reflux for 30 minutes and thereafter cooled to 5° C. Ethyl 2-cyano-3-(3-methyl-2-pyridylamino)acrylate (10.40, 45.0 mmol; from step IIa above) was added and the reaction mixture was heated to reflux for 18 hours. The reaction mixture was allowed to cool and the THF was removed under reduced pressure. The residue was treated with ice water (210 mL) and acidified with 6 M HCl to pH 3. The solid material was collected by filtration and recrystallised from DMF to give the subtitle product (4.61 g, 44.9%).

LC-MS (M+H$^+$) 229.1. $^1$H NMR (DMSO-d6) δ: 9.21 (s, 1H, CH), 9.16-9.11 (m, 1H, CH), 8.13-8.07 (m, 1H, CH), 7.58-7.51 (m, 1H, CH), 2.62 (s, 3H, CH$_3$).

(IIc) 9-Methyl-3-(1H-tetrazol-5-yl)-4H-pyrido[1,2-a]pyrimidin-4-one (Pemirolast), Sodium Salt 1M NaOH (20.30 mL, 20.3 mmol) was added dropwise to a suspension of 9-methyl-3-(1H-tetrazol-5-yl)-4H-pyrido[1,2-a]pyrimidin-4-one (4.60 g, 20.1 mmol; from step IIb above) in water (115 mL). The reaction mixture was diluted with 100 mL of water and heated to 50° C. for 2 minutes. The solution was filtered and the water removed by lyophilisation. The crude product (6.13 g) was divided into portions and recrystallized from water:ethanol in different ratios to give pure title compound.

COMPARATIVE EXAMPLE 5

Recrystallisation of Pemirolast Sodium According to the Method of U.S. Pat. No. 4,122,274

In U.S. Pat. No. 4,122,274, it is stated that the crude title product (pemirolast sodium) was recrystallised from water:ethanol to give pure title product. It is not clear from this level of detail what the ratio of water:ethanol employed was, so several experiments were performed with a view to reproducing the prior art technique.

(i) Crude sodium salt of pemirolast (480 mg; from Example 4, method (I) above) was recrystallised from water and ethanol (95%) in a 1:1 ratio. The Na salt of pemirolast (480 mg, 1.92 mmol) was dissolved in H$_2$O (8 mL) at 70° C. and EtOH 95% (8 mL) was added. The clear solution was allowed to reach room temperature and the solid material formed was filtered off, washed with a small amount of ethanol and dried in vacuum to give 316 mg of pure sodium salt.

(ii) Crude sodium salt of pemirolast (500 mg; from Example 4, method (II) above) was dissolved in water (4.9 mL) at 70° C. Thereafter EtOH 95% (ca. 4.0 mL) was added at 70° C. until a solid started to form. Another 0.1 mL of water was added to get everything into solution. The solid material formed upon cooling was collected by filtration and dried under vacuum to give 348 mg of pure sodium salt.

(iii) Crude sodium salt of pemirolast (300 mg; from Example 4, method (II) above) was recrystallised from water:ethanol (1:1 ratio; 10 mL) at 70° C. The solid material formed upon cooling was collected by filtration and dried under vacuum to give 174 mg of pure sodium salt.

(iv) Crude sodium salt of pemirolast (300 mg; from Example 4, method (II) above) was recrystallised from water:ethanol (9:1 ratio, 4 mL) at 70° C. The solid material formed upon cooling was collected by filtration and dried under vacuum to give 219 mg of pure sodium salt.

All four samples of pure pemirolast sodium salt had the same physico-chemical properties (Raman spectra and NMR):

$^1$H NMR (D$_2$O) δ: 8.86-8.80 (m, 1H, CH), 8.57 (s, 1H, CH), 7.68-7.59 (m, 1H, CH), 7.22-7.13 (m, 1H, CH), 2.39 (s, 3H, CH$_3$).

Figure 3:
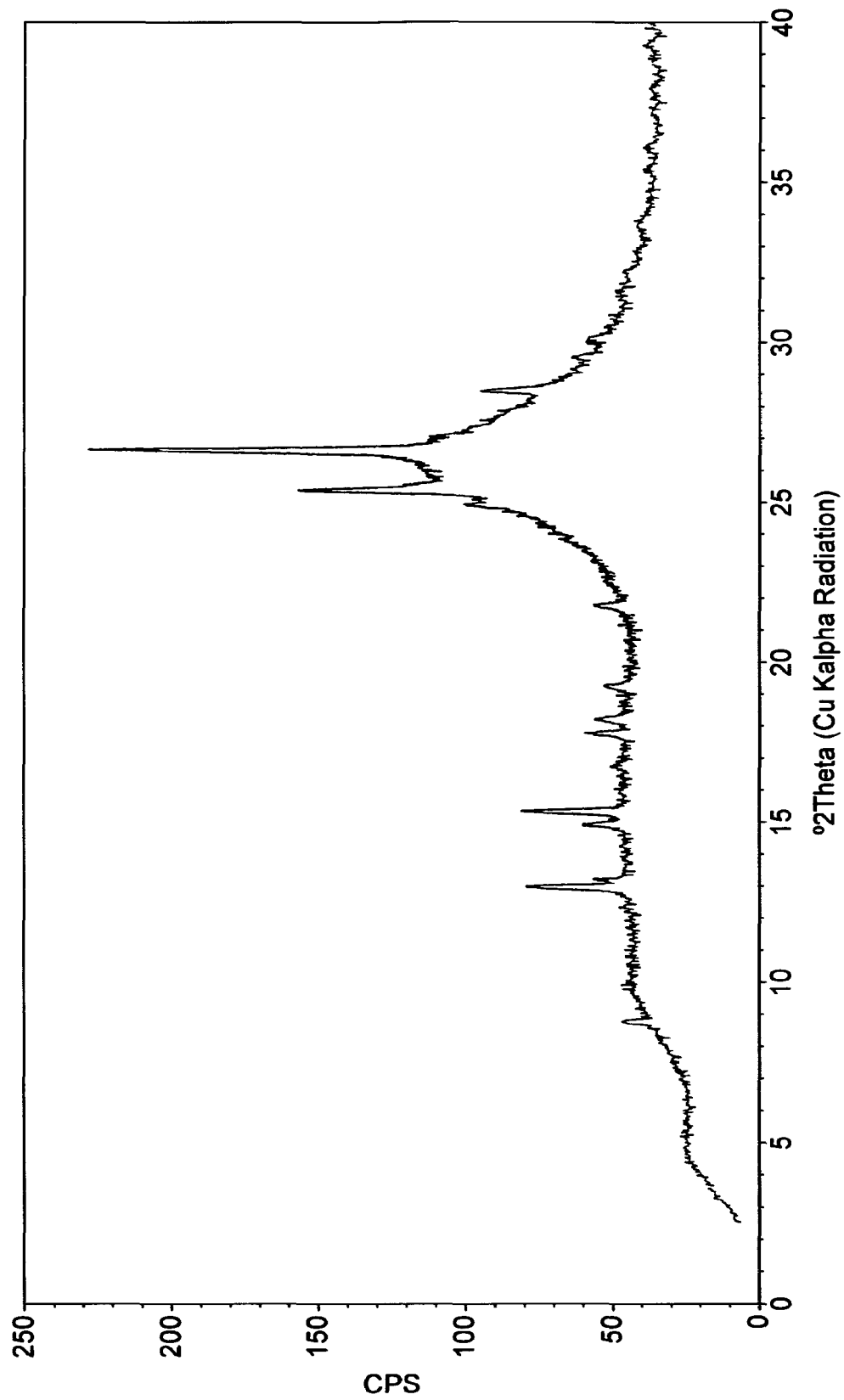
FIG. 3 shows a powder X-ray diffractogram for the crystalline form of pemirolast sodium obtained by way of Example 5.

The PXRD pattern (measured in respect of Example 5(i) above) is shown in FIG. 3. It was concluded from this that this form of the sodium salt is an amorphous material mixed with a crystalline fraction.

Figure 4:
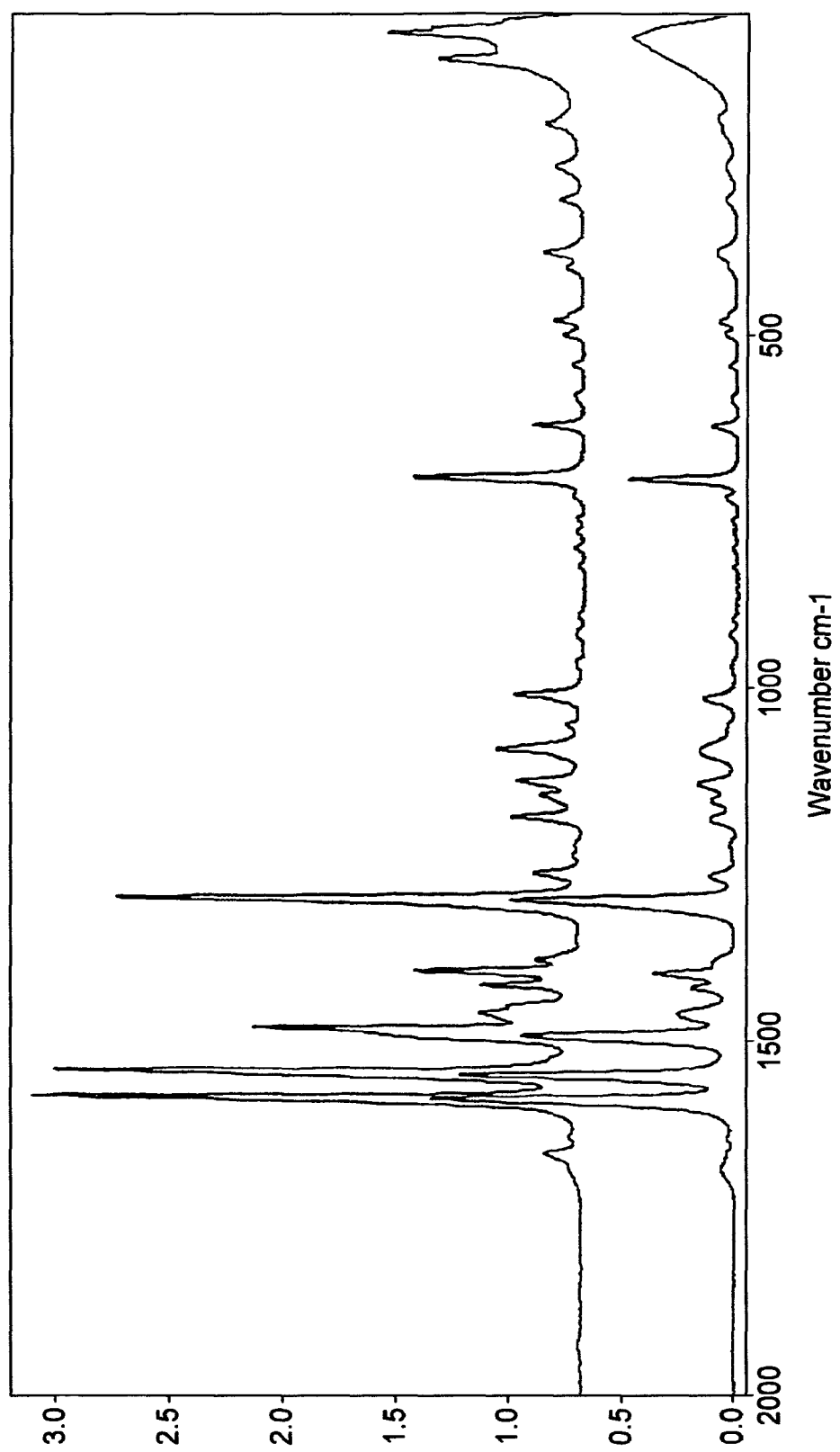
FIG. 4 shows an FT-Raman spectra for the crystalline form of pemirolast sodium obtained by way of Example 5 at different time points (after preparation (lower trace) and about a month later (upper trace)).

The Raman spectrum was recorded directly after recrystallisation. All samples were then stored under ambient conditions on a shelf in a fume hood. About a month later, a Raman spectrum was recorded, which was significantly different to that recorded earlier. This is shown in FIG. 4, where the lower spectrum accords to the earlier measurement and the upper spectrum accords to the later measurement. In the light of these results, it was concluded that the prior art amorphous form of pemirolast sodium is physically unstable.

The amorphous material was also prepared by drying of the form obtained in accordance with Example 11 below at 40° C. and reduced pressure for 40 hours to yield 12 g of a pale yellow cotton-like amorphous solid.

GENERAL PROCEDURES FOR EXAMPLES 6 TO 16

TGA was measured using a Thermal Advantage TGA Q50001R (TA instrument) module. The samples (ca. 10-16 mg) was placed onto the platinum pan (100 HI) and heated from 25 to 350° C. at a heating rate of 10° C./min under nitrogen purge.

Microscopy was performed with a Nikon SMZ800 microscope equipped with plane polarised light.

Karl Fischer coulometric titration was carried out on an apparatus equipped with a drying oven (set to 290° C.).

DSC was studied using a Thermal Advantage DSC Q1000 (TA instruments) equipped with a refrigerated cooling system. The instrument had been calibrated for temperature and enthalpy using indium. About 2-3 mg of the sample was accurately weighed into non-hermetic aluminium pan and crimped. The sample was scanned from 25 to 275° C. at a heating rate of 10° C./min under continuous nitrogen purge (50 mL/min).

PXRD patterns for samples were collected using a Siemens D5000 powder diffractometer with CuK radiation (1.540 56 Å). The tube voltage and amperage were set at 40 kV and 40 mA, respectively. The divergence slit and antiscattering slit settings were variable for the illumination on the 20 mm sample area. Each sample was scanned between 5 and 40° in 2θ with a step size of 0.02°. The measurement time per step was 1 second and the sample stage was spun at 30 rpm (powder samples) or not spun (tablets) during analysis. Small volume zero background holders were also used. The instrument was previously calibrated using a silicon standard. (Forms prepared in accordance with the Examples below showed "essentially" the same PXRD diffraction patterns as other Examples disclosed below, when it was clear from the relevant patterns (allowing for experimental error) that the same crystalline form had been formed. Thus, limits of experimental error for PXRD distance values may be in the range ±2 or thereabouts on the last decimal place as employed in any part of this specification.)

HPLC-UV (Example 16) was performed using an Agilent XDB C18 50×4.6, 1.8 μm column. The temperature of the column oven was 40.0° C., the flow rate was 1 mL/min, detection UV/VIS at 370.0 nm. The injection volume was 10 μL. HPLC-UV (Example 10) was performed using a Chromolith Performance RP-18 100×4.6 mm Column (Merck), the column oven was set at ambient temperature, the flow rate was 3 mL/min, detection UV at 254 nm. Both HPLC methods used a mobile phase A of 0.1% TFA (aq.) and a mobile phase B of acetonitrile.

EXAMPLE 6

Pemirolast Sodium Hemihydrate

Pemirolast free acid (1 g; prepared from the corresponding potassium salt (Chemtronica AB, Stockholm, Sweden) by dissolution in water and acidification with acetic acid, whereupon the precipitated free acid was filtered off and dried) was suspended in a series of selected organic solvents or solvent mixtures (15 mL), as set out in Table 3 below. The resultant slurry was thereafter heated to 50-60° C. and a salt former (1 eq. of sodium hydroxide (50% aqueous solution or an 8% solution in methanol), or sodium ethoxide (21% solution in ethanol)) was added. Partial dissolution of the solid was observed. However, within a few seconds, a new precipitate was obtained and the slurry became thicker. The slurry was equilibrated for 1-2 hours at 50-60° C. and then cooled to room temperature and filtered. The solid was dried at room temperature and atmospheric pressure in 1-2 days.

TABLE 3

| Solvent System | Salt former |
| --- | --- |
| Ethanol | Sodium hydroxide (50% aq.) |
| Methanol | Sodium hydroxide (in methanol) |
| Ethanol | Sodium ethoxide |
| Isopropanol | Sodium ethoxide |
| Ethanol:water (90:10) | Sodium ethoxide |

The crystals were analyzed by PXRD. The relevant spectra were essentially the same as that exhibited by the form obtained according to Example 10 below (and Example 1 above).

The crystals obtained from the methanol and isopropanol crystallisations above were analysed by DSC and TGA and were all confirmed to be hemihydrates.

COMPARATIVE EXAMPLE 7

Pemirolast Sodium Heptahydrate

Pemirolast free acid (3 g; prepared as described in Example 6 above) was suspended in water (30 mL) and the slurry was heated to ca. 50° C. 1 eq. of 50% NaOH (aq)) was added, whereupon a clear solution was obtained. The solution was cooled down. At a solution temperature of about 40° C., the salt started to crystallize and a very thick slurry was obtained. To dilute the slurry additional water (80 mL) was added. The slurry was finally cooled down to 0° C., equilibrated for 1 hour and subsequently filtered. The solid was dried at room temperature and atmospheric pressure for 1-2 days to give 4.04 g of the title compound.

The crystals were analyzed by PXRD. The relevant spectrum was essentially the same as that exhibited by the form obtained according to Example 11 below.

EXAMPLE 8

Pemirolast Sodium Hemihydrate

A sample of pemirolast sodium heptahydrate (3.5 g, obtained in accordance with the method described in Example 7 above) was suspended in water (3.0 mL) and heated to approximately 80° C. The slurry was filtered at this temperature, and then dried at room temperature and atmospheric pressure. The yield was 1.3 g.

The crystals were analyzed by PXRD. The relevant spectrum was essentially the same as that exhibited by the form obtained according to Example 10 below (and Example 1 above).

EXAMPLE 9

Pemirolast Sodium Hemihydrate (a) Pemirolast

The free acid was prepared from pemirolast potassium (15.8 g; Chemtronica AB) by dissolution in a mixture of water (100 mL) and THF (80 mL) at room temperature and acidification with acetic acid (1 eq.; 17.5 g; 20% aq.). Firstly, ca. 1 mL of acetic acid was added and the obtained thin slurry was equilibrated for about 30 minutes. Thereafter the rest of the acetic acid was added slowly. The resultant thick slurry was diluted with water (50 mL) and equilibrated for 2 hours and then filtered and washed with water. The resultant solid was dried at 40° C. and under reduced pressure for 5-10 hours to yield 7.5 g of sub-title compound.

(b) Pemirolast Sodium Hemihydrate

The free acid (1 g; from step (a) above) was suspended in a mixture of ethanol (13.5 mL) and water (1.5 mL) and the suspension was heated to 60° C. Sodium ethoxide (1 eq.; 1.43 g; 21% solution in ethanol) was added, whereupon partial dissolution of the solids resulted in a slurry. The sodium salt crystallized immediately, forming a new slurry. The slurry was equilibrated at 60° C. for about 1 hour and thereafter cooled down to 20-25° C. and filtered. The filter-cake was washed with ethanol and dried at room temperature and atmospheric pressure for 1-2 days to yield 0.99 g of the title compound.

The crystals were analyzed by PXRD. The relevant spectrum was essentially the same as that exhibited by the form obtained according to Example 10 below (and Example 1 above).

EXAMPLE 10

Pemirolast Sodium Hemihydrate—Large Scale Production (a) Pemirolast

Pemirolast potassium (190 g; 0.71 mol; Chemtronica AB) was dissolved in a mixture of water (2,500 mL) and THF (1,400 mL) with stirring for 1 h at room temperature. The mixture was then clear-filtered, and acetic acid (43 g, 0.72 mol) in water (400 mL) was added in 2 portions. Firstly, approximately 50 mL of the mixture was added and the resultant slurry stirred for 30 minutes. Then, the rest of the acetic acid solution was added slowly. The resultant slurry was equilibrated over 2 hours, filtered and washed with water. The sub-title compound was air-dried overnight and then dried in a vacuum oven at 40° C. for 24 hours. The yield was 164 g (white solid, hard clumps).

(b) Pemirolast Sodium Hemihydrate

The free acid (45.5 g, 0.2 mol; from step (a) above) was suspended in ethanol (630 mL) and the mixture was heated to 57° C. (internal temperature). Sodium hydroxide (8.0 g, 0.2 mol) in water (72 mL) was added. Partial dissolution of the solids resulted in a slurry almost immediately, which was followed by crystallization. The slurry was equilibrated at 57° C. over 1 hour, then cooled to 20-25° C. and filtered. The filter-cake was washed with ethanol and dried in vacuo at room temperature for 48 h. The yield of the title compound was 45 g, obtained as a pale-yellow powder. The purity was determined to be >99% by HPLC-UV.

Figure 5:
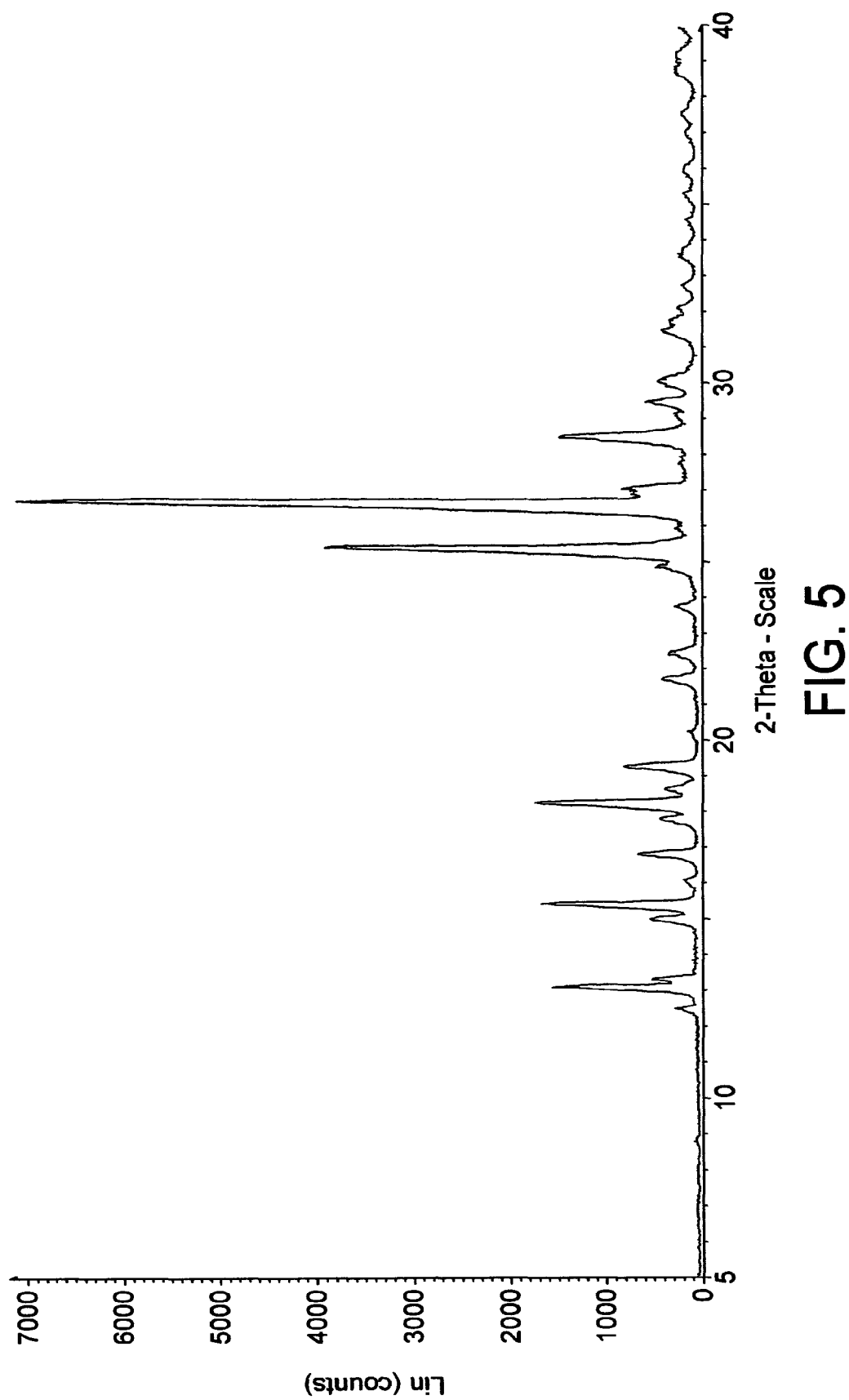
FIG. 5 shows a powder X-ray diffractogram for the crystalline form of pemirolast sodium hemihydrate obtained by way of Example 10.
Figure 6:
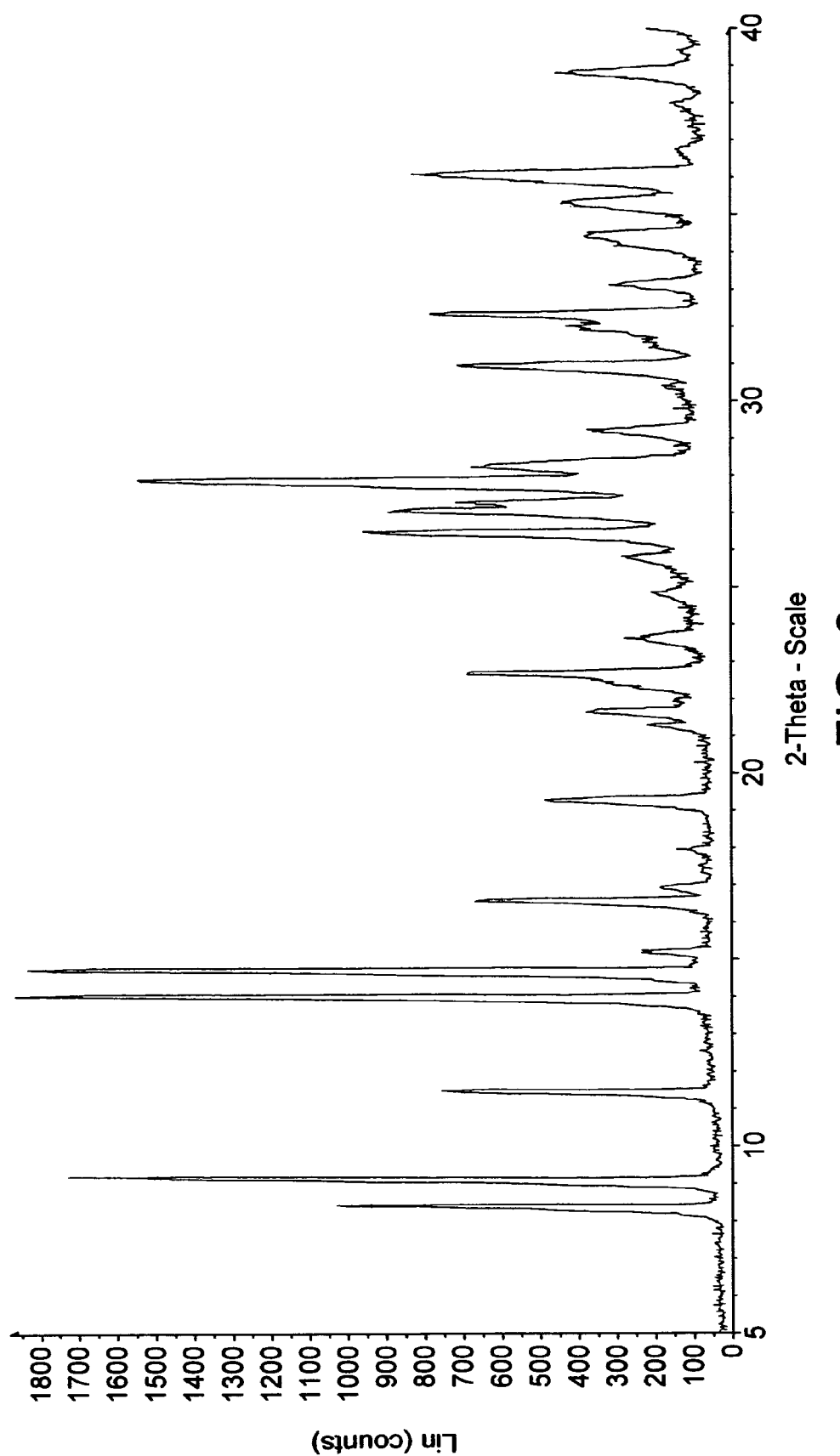
FIG. 6 shows a powder X-ray diffractogram for the crystalline form of pemirolast sodium heptahydrate obtained by way of Example 11.

The crystals were analysed by PXRD. The relevant spectrum is shown in FIG. 5 and the major peaks are tabulated in Table 4 below. (It is clear from this analysis that the form obtained according to Example 10 is the same as that obtained according to Examples 1 and 2, but that the former samples may have comprised starting material (pemirolast free acid), impurities and/or by-products.)

TABLE 4

| Angle (2-Theta °) | d value (Angstrom) | Relative Intensity (%) |
|---|---|---|
| 13.01 | 6.80 | 21.9 |
| 14.93 | 5.93 | 7.7 |
| 15.33 | 5.77 | 23.5 |
| 16.76 | 5.29 | 9.3 |
| 18.19 | 4.87 | 24.6 |
| 19.24 | 4.61 | 11.3 |
| 25.32 | 3.52 | 55.1 |
| 26.55 | 3.35 | 100.0 |
| 27.00 | 3.30 | 11.7 |
| 28.45 | 3.14 | 20.8 |
| 29.45 | 3.03 | 8.2 |

COMPARATIVE EXAMPLE 11

Pemirolast Sodium Heptahydrate—Large Scale Production

Pemirolast free acid (80 g, 0.35 mol; see Example 10(a) above) was suspended in water (3 L) and heated to 50° C. Sodium hydroxide (14 g, 0.35 mol) in water (14 g) was added and the resultant solution was clear filtered. The solution was cooled down to 20° C. The product started to crystallize spontaneously at about 25-28° C. The slurry was equilibrated at 20° C. for 30 minutes, then cooled down to 0° C. The slurry was equilibrated at 0° C. for 2 hours, filtered and washed with ice-cold water (400 mL). Residual wet material was dried at atmospheric pressure, 45° C. and 75% relative humidity. Crystals melted together giving candy-like material. This material was dissolved in 2.5 L water at 50° C. and the crystallization procedure repeated. The resultant precipitate was filtered, dried by sucking air through it for approximately 40 minutes and then dried at atmospheric pressure, 25° C. and 60% relative humidity. The yield was 80 g of a pale yellow solid.

Figure 7:
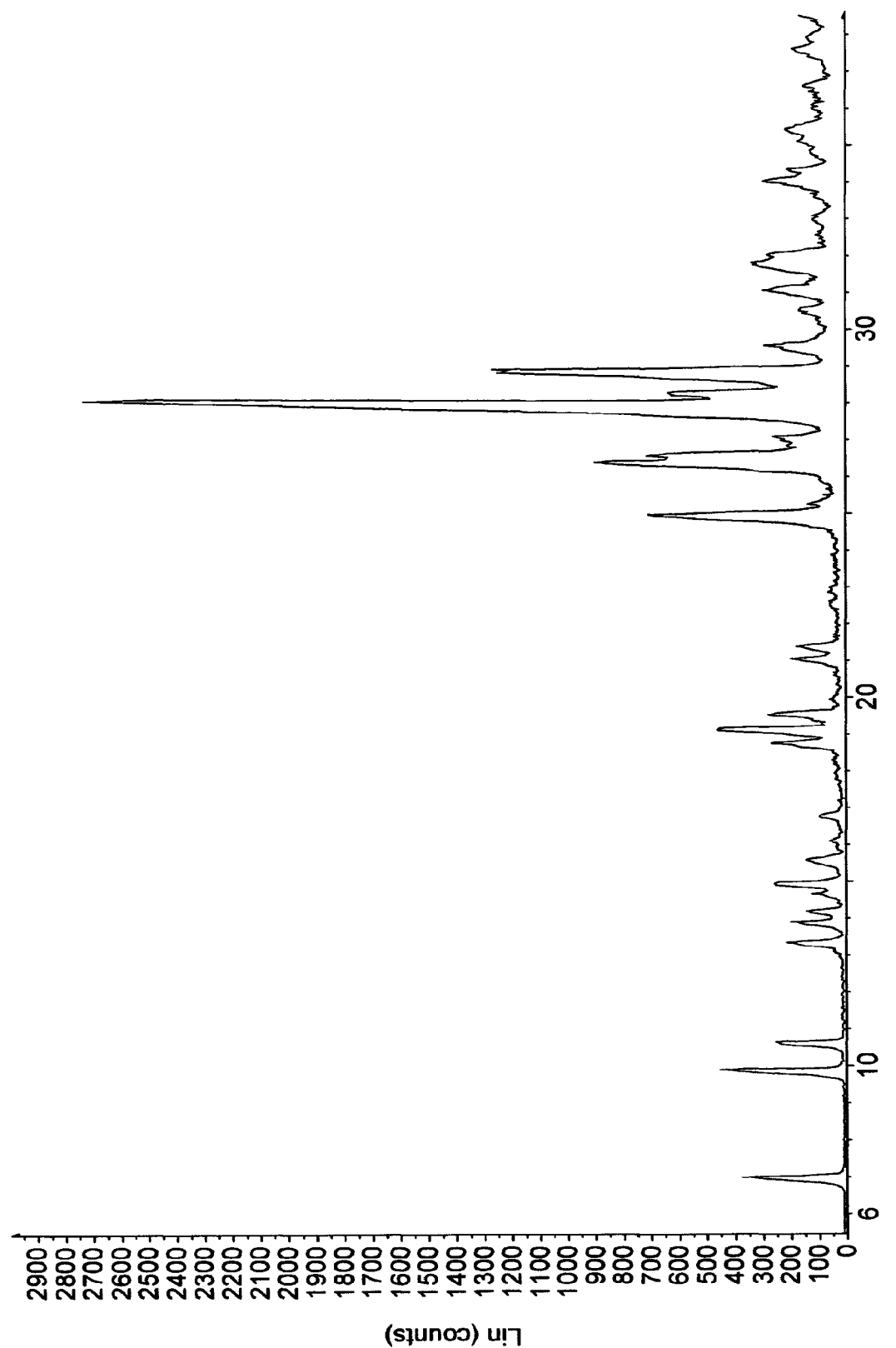
FIG. 7 shows a powder X-ray diffractogram for the additional crystalline form of pemirolast sodium obtained by way of Example 14.

The PXRD pattern of the form obtained by way of Example 11 is shown in FIG. 7 and the major peaks are tabulated in Table 5 below.

TABLE 5

| Angle (2-Theta °) | d value (Angstrom) | Relative Intensity (%) |
|---|---|---|
| 8.33 | 10.61 | 55.3 |
| 9.04 | 9.78 | 92.5 |
| 11.36 | 7.78 | 40.5 |
| 13.86 | 6.38 | 100.0 |
| 14.56 | 6.08 | 98.2 |
| 15.13 | 5.85 | 12.3 |
| 16.48 | 5.37 | 35.7 |
| 16.88 | 5.25 | 9.8 |
| 19.23 | 4.61 | 26.0 |
| 21.25 | 4.18 | 10.7 |
| 21.62 | 4.11 | 20.1 |
| 22.34 | 3.98 | 16.7 |
| 22.63 | 3.93 | 36.8 |
| 23.58 | 3.77 | 14.7 |
| 24.76 | 3.59 | 11.0 |
| 25.72 | 3.46 | 15.1 |
| 26.36 | 3.38 | 51.3 |
| 26.94 | 3.31 | 47.8 |
| 27.18 | 3.28 | 38.3 |
| 27.72 | 3.22 | 82.3 |
| 28.15 | 3.17 | 36.1 |
| 29.13 | 3.06 | 19.0 |
| 30.87 | 2.89 | 38.0 |
| 31.48 | 2.84 | 10.7 |
| 31.94 | 2.80 | 22.8 |
| 32.27 | 2.77 | 42.0 |
| 33.10 | 2.70 | 16.8 |
| 34.18 | 2.62 | 15.4 |
| 34.43 | 2.60 | 20.3 |
| 35.31 | 2.54 | 23.4 |
| 36.04 | 2.49 | 44.5 |
| 38.80 | 2.32 | 24.1 |

DSC (on a sample prepared previously, not by way of Example 11) showed two endotherms, one at 71.1° C. and one at 90.2° C.

EXAMPLE 12

Pemirolast Sodium Hemihydrate

Pemirolast sodium hemihydrate (0.35 g; obtained in accordance with the method described in Example 10) was added to water (0.8 g). The sample was heated to 85-90° C. The resultant clear solution was cooled to 75° C. and portions of 2 mL of hot ethanol (75° C.) were added every 5 minutes. The crystallization started after addition of 6 mL. An additional 6 mL was added over 10 minutes. The sample was cooled to 20° C., filtered and dried at room temperature and atmospheric pressure overnight to yield 0.19 g of the title compound. The isolated precipitate was inspected under a light microscope equipped with plane-polarized light and analysed by PXRD. The relevant spectrum was essentially the same as that exhibited by the form obtained according to Example 10 (and Example 1) above.

EXAMPLE 13

Crystallisation Experiments

Pemirolast sodium hemihydrate (0.2-0.4 g; obtained in accordance with the method described in Example 10) was added to 10 mL of ethanol and water, as well as mixtures thereof in ratios of 80:20, 60:40, 40:60 and 20:80. The samples were heated to 50-70° C. A clear solution was obtained in 0:100, 20:80, 40:60 and 60:40 (ethanol:water ratios). In the 80:20 and 100:0 (ethanol:water ratios) undissolved crystals were allowed to sediment and the clear solutions were decanted. The clear solutions were then left to cool down slowly to 20° C.

A visual inspection of the precipitates obtained was conducted under a light microscope equipped with plane-polarized light. Based upon the known physical appearance of fully characterised crystalline forms obtained according to the method described in Example 10 above (pemirolast sodium hemihydrate; which appears as cube crystals) or Example 11 above (pemirolast sodium heptahydrate; which appears as needle-like crystals), a judgement was made as to which of those two crystalline forms had been obtained.

After that inspection has been carried out, the samples were again heated until complete dissolution was observed (in all cases). The solutions were again left to slowly cool down to ca. 35° C. and were seeded with a 1:1 mixture of pemirolast sodium hemihydrate crystals (obtained in accordance with the method described in Example 10 above) and pemirolast sodium heptahydrate crystals (obtained in accordance with the method described in Example 11 above). The samples were finally cooled down to 20° C. and the precipitates obtained were inspected under a light microscope equipped with plane-polarized light as described above.

The results are tabulated in Table 6 below.

TABLE 6

| Ethanol:water ratio (% v/v) | Dissolution Temp. (° C.) | Final Temp. (° C.) | Seeding | Crystal form Obtained |
|---|---|---|---|---|
| 0:100 | 50 | 20 | No | Heptahydrate |
|  |  |  | Yes | Heptahydrate |
| 20:80 | 50 | 20 | No | Heptahydrate |
|  |  |  | Yes | Heptahydrate |
| 40:60 | 50 | 20 | No | Heptahydrate |
|  |  |  | Yes | Heptahydrate |
| 60:40 | 60 | 20 | No | Heptahydrate |
|  |  |  | Yes | Heptahydrate |
| 80:20 | 70 | 20 | No | Heptahydrate |
|  |  |  | Yes | Heptahydrate |
| 100:0 | 70 | 20 | No | Hemihydrate |
|  |  |  | Yes | Hemihydrate |

Following this, pemirolast sodium hemihydrate (0.2-0.4 g; obtained in accordance with the method described in Example 10) was added to 10 mL of ethanol:water mixtures in ratios of 80:20, 85:15, 90:10 and 95:5. The samples were heated to 50-70° C. The undissolved crystals were allowed to sediment and the clear solutions were decanted. The clear solutions were then left to cool down slowly to 20° C. and the obtained precipitates were inspected under a light microscope equipped with plane-polarized light as described above.

After that inspection has been carried out, the samples were again heated until complete dissolution was observed (in all cases). The solutions were left to slowly attain a temperature of ca. 50° C. and then seeded with crystals of the opposite form to that obtained in the experiments performed without seeding. The samples were finally cooled down to 20° C. and the obtained precipitates were inspected under a light microscope equipped with plane-polarized light as described above.

The results are tabulated in Table 7 below.

TABLE 7

| Ethanol:water ratio (% v/v) | Dissolution Temp. (° C.) | Final Temp. (° C.) | Seeding | Crystal form Obtained |
|---|---|---|---|---|
| 80:20 | 70 | 20 | No | Heptahydrate |
|  |  |  | With hemihydrate | Heptahydrate |
| 85:15 | 70 | 20 | No | Heptahydrate |
|  |  |  | With hemihydrate | Heptahydrate |
| 90:10 | 70 | 20 | No | Hemihydrate |
|  |  |  | With heptahydrate | Hemihydrate |
| 95:5 | 70 | 20 | No | Hemihydrate |
|  |  |  | With heptahydrate | Hemihydrate |

The conclusion from this experiment is that pemirolast sodium hemihydrate may be prepared by partial dissolution in an organic solvent in the presence of no more than about 10% water.

EXAMPLE 14

Stability Study

To determine the relative stability of pemirolast sodium obtained in accordance with the method described in Example 10 (hemihydrate), Example 11 (heptahydrate) and Example 5 (amorphous form) at different moisture levels, a stability study was performed.

The study was performed under four different storage conditions with different moisture levels and temperatures, 40° C./75% RH, 25° C./60% RH, room temperature/10-20% RH, and room temperature/>90% RH. The substances were stored open in glass beakers and samples were withdrawn periodically for analysis (time zero, 1 week and 4 weeks).

At the time intervals mentioned, the visual appearance was inspected by (a) placing a spatula of substance on a white background, munktell filter (no smearing or crushing of the substances was performed), and (b) by microscopy equipped with plane polarized light. The water content was also analysed using Karl Fischer titration. PXRD was conducted at time zero and at 4 weeks.

The study demonstrated that the hemihydrate form is stable (solid phase) when stored at a relative humidity of 60% and less (down to 10-20% RH investigated) for up to 4 weeks. The visual appearance, including inspection under light microscope remained unchanged under these storage conditions. Water analysis (Karl Fisher) demonstrated unchanged results under these conditions (2.8%+/−0.2).

At 75% RH and above the hemihydrate converted to a previously unknown solid state form (as demonstrated by the PXRD pattern shown in FIG. 7, the major peaks of which are tabulated in Table 8 below).

TABLE 8

| Angle (2-Theta °) | d value (Angstrom) | Relative Intensity (%) |
|---|---|---|
| 6.92 | 12.76 | 13.7 |
| 8.04 | 10.99 | 0.2 |
| 9.77 | 9.05 | 16.6 |
| 10.53 | 8.40 | 9.1 |
| 13.20 | 6.70 | 7.8 |
| 13.78 | 6.42 | 7.1 |
| 14.06 | 6.29 | 5.0 |
| 14.57 | 6.08 | 4.1 |
| 14.81 | 5.97 | 9.3 |
| 15.46 | 5.73 | 4.9 |
| 16.02 | 5.53 | 2.0 |
| 16.71 | 5.30 | 3.4 |
| 17.81 | 4.98 | 1.1 |
| 18.20 | 4.87 | 1.6 |
| 18.70 | 4.74 | 9.5 |
| 19.06 | 4.65 | 16.7 |
| 19.49 | 4.55 | 10.1 |
| 19.88 | 4.46 | 1.9 |
| 20.99 | 4.23 | 6.9 |
| 21.36 | 4.16 | 6.3 |
| 22.51 | 3.95 | 2.0 |
| 22.90 | 3.88 | 1.9 |
| 23.82 | 3.73 | 1.7 |
| 24.90 | 3.57 | 25.9 |
| 26.33 | 3.38 | 32.8 |
| 26.53 | 3.36 | 26.1 |
| 27.01 | 3.30 | 9.2 |
| 27.86 | 3.20 | 100.0 |
| 28.23 | 3.16 | 23.2 |
| 28.81 | 3.10 | 46.1 |
| 29.54 | 3.02 | 10.6 |
| 30.54 | 2.92 | 5.9 |
| 31.10 | 2.87 | 10.7 |
| 31.81 | 2.81 | 12.2 |
| 32.02 | 2.79 | 10.1 |
| 33.04 | 2.70 | 4.0 |
| 34.07 | 2.63 | 10.9 |
| 34.36 | 2.61 | 7.6 |
| 34.88 | 2.57 | 4.5 |
| 35.48 | 2.53 | 7.7 |
| 36.12 | 2.49 | 4.1 |
| 36.70 | 2.45 | 5.3 |
| 37.64 | 2.39 | 6.7 |
| 38.00 | 2.37 | 4.8 |
| 38.69 | 2.33 | 6.9 |
| 39.17 | 2.30 | 5.0 |

This form contains approximately the same amount of water as the heptahydrate (approximately 30% (w/w)).

The heptahydrate form, on the other hand, was only stable at one condition investigated, 60% RH, for up to 4 weeks. Under dry conditions (10-20% RH), the heptahydrate form was converted to the hemihydrate form. At higher humidity levels (75% RH) the sample converted partially to the new solid state form mentioned above, and characterised in FIG. 7. However, at 90% RH no signs of phase transitions were observed.

The amorphous form crystallized under storage conditions of 60% RH and above while under dry conditions 10-20% RH, it remains amorphous. At 60% RH and above, two solid forms appeared after storage for 4 weeks, the heptahydrate and the new solid state form mentioned above, and characterised in FIG. 7 and in Table 8 above.

EXAMPLE 15

Tablet Feasibility Study (A) 5 mg Tablets

A placebo batch, 81002-1002-16 was first produced and used for adjustments of the rotary tablet press (Korsch PH106).

Then a batch of 1000 hemihydrate-containing tablets was produced with the excipients tabulated in Table 9 below. Temperature and relative humidity were monitored during the study. In this case, the RH was 12.7%. The hemihydrate was obtained in accordance with the methodology described in Example 10 above and was sieved prior to dry mixing by passing through a 500 µm sieve. Mixing with the excipients listed below (apart from magnesium stearate) was carried out in a Turbula mixer for 10 minutes. After this, magnesium stearate was passed through a 500 µm sieve and added to the mixture, followed by another 2 minutes of mixing. Tablets were produced on a rotary tablet press (Korsch PH106) using circular concave punches with a diameter of 7 mm at 25 rpm. Three compression forces were evaluated, low, medium and high (approximately 3, 4 and 7 kN, respectively).

TABLE 9

| Material | Weight per tablet (mg) | Weight (%) | Weighed (g) |
|---|---|---|---|
| Hemihydrate | 5.0[1] | 3.3 | 5.05 |
| Isomalt DC 100 (Palatinit GmbH, Germany) | 86.3 | 57.5 | 86.30 |
| Microcrystalline cellulose (MCC) PH-102 (Avicel, FMC Int., Ireland) | 57.6 | 38.4 | 57.64 |
| Magnesium stearate (Peter Greven Nederland CV, Netherlands) | 1.1 | 0.73 | 1.15 |
| Target weight | 150 mg | | |

[1]Compensated for purity, water content and switch from K to Na salt.

The same methodology was employed to produce a batch of 1000 heptahydrate-containing tablets with the following excipients (see Table 10 below) at a RH of 12.2%. The heptahydrate was obtained in accordance with the methodology described in Example 11 above.

TABLE 10

| Material | Weight per tablet (mg) | Weight (%) | Weighed (g) |
|---|---|---|---|
| Heptahydrate | 7.1[1] | 4.7 | 7.11 |
| Isomalt DC 100 | 86.3 | 57.5 | 86.32 |
| MCC PH-102 | 55.5 | 37.0 | 55.52 |
| Magnesium stearate | 1.1 | 0.73 | 1.12 |
| Target weight | 150 mg | | |

[1]Compensated for purity, water content and switch from K to Na salt.

(B) 0.2 mg Mini-Tablets

The same methodology as described in (A) above was employed to produce two separate batches of 5000 hemi- and heptahydrate-containing tablets with the following excipients (Tables 11 and 12 below) at a RH of 11.6% (hemihydrate) and 12.2% (heptahydrate). As before, a placebo was first produced and used for tablet press adjustments. Circular concave punches with a diameter of 3 mm were employed on the tablet press, with one compression force (approximately 400 N).

TABLE 11

| Material | Weight per tablet (mg) | Weight (%) | Weighed (g) |
|---|---|---|---|
| Hemihydrate | 0.2[1] | 2.0 | 1.01 |
| Isomalt DC 100 | 5.76 | 57.6 | 28.80 |

TABLE 11-continued

| Material | Weight per tablet (mg) | Weight (%) | Weighed (g) |
|---|---|---|---|
| MCC PH-102 | 3.96 | 39.6 | 19.82 |
| Magnesium stearate | 0.08 | 0.8 | 0.41 |
| Target weight | 10 mg | | |

TABLE 12

| Material | Weight per tablet (mg) | Weight (%) | Weighed (g) |
|---|---|---|---|
| Heptahydrate | 0.28[1] | 2.8 | 1.41 |
| Isomalt DC 100 | 5.76 | 57.6 | 28.81 |
| MCC PH-102 | 3.88 | 38.8 | 19.42 |
| Magnesium stearate | 0.08 | 0.8 | 0.43 |
| Target weight | 10 mg | | |

[1]Compensated for purity, water content and switch from K to Na salt.

(C) 30 mg Tablets

A similar methodology to that described in (A) above was employed to produce two separate batches of 250 hemi- and heptahydrate-containing tablets with the following excipients (Table 13 and 14 below) at a RH of 8.0% (hemihydrate) and 10.2% (heptahydrate).

The active substance was firstly sieved through a 250 μm sieve, instead of the 500 μm sieve, in an attempt to improve content uniformity. The active substance was then pre-mixed by hand with MCC. Flat circular punches with a diameter of 6 mm were employed on the tablet press. For the hemihydrate formulation, containing approximately 31% of active substance (which was changed from what was planned due to a shortage of active substance), two compression forces were employed, 5 and 14 kN. For the heptahydrate formulation, containing approximately 47% active substance, the lack of powder flow only rendered one compression force that could be evaluated (approximately 2 kN). This compaction force was highly variable due to the flow properties of the heptahydrate formulation.

TABLE 13

| Material | Weight per tablet (mg) | Weight (%) | Weighed (g) |
|---|---|---|---|
| Hemihydrate | 30.0[1] | 33.3 | 13.78* |
| Isomalt DC 100 | 32.0 | 35.6 | 16.02 |
| MCC PH-102 | 27.3 | 30.3 | 13.71 |
| Magnesium stearate | 0.7 | 0.78 | 0.38 |
| Target weight | 90 mg | | |

TABLE 14

| Material | Weight per tablet (mg) | Weight (%) | Weighed (g) |
|---|---|---|---|
| Heptahydrate | 42.6[1] | 47.3 | 10.60 |
| Isomalt DC 100 | 25.0 | 27.8 | 6.26 |
| MCC PH-102 | 21.7 | 24.1 | 5.43 |
| Magnesium stearate | 0.7 | 0.78 | 0.19 |
| Target weight | 90 mg | | |

[1]Compensated for purity, water content and switch from K to Na salt.
*Due to shortage of API the dose is compensated by increasing the total tablet weight by 8% to 97.2 mg.

For all tablets, friability and crushing resistance tests were conducted according to standard methodology (Ph. Eur. 6.0, 2.9.7 and 2.9.8, respectively, with the exception that the crushing resistance results are presented in kp rather than N according to the Ph. Eur.). PXRD was also performed on the 30 mg tablets after tabletting on both crushed and intact tablets.

Results

The heptahydrate was observed to resemble sticky/soapy flakes and was found to be quite hard to pass through the 500 μm sieve. After sieving, some material remained in the sieve. This was not experienced in the case of the hemihydrate.

In most cases, acceptable compression force/crushing strength curves were observed, as were reasonable weight variations, friability and content uniformity.

However, for the 30 mg tablets, the tabletting process for the heptahydrate formulation was not straightforward, mainly due to poor flow properties of the powder mix (solid), resulting in high tablet weight variability. This variation also gave rise to variations in compression force (since this is adjusted to a fixed distance between the lower and upper punches—less powder in the die with a fixed distance between the punches results in a lower compression force). Also adhesion to the punch surfaces was experienced with damaged tablets surfaces, resulting in poor friability.

In view of the endotherms observed (and reported in Example 11 above) by DSC for the heptahydrate, it was expected that this may limit the ability of that polymorph to form tablets by compression (given that internal temperatures of 70° C. can easily be reached during the compression process). It was therefore decided to analyse the 30 mg tablets by PXRD as stated above. PXRD analysis showed that no phase transitions occurred during tabletting for either the hemihydrate or the heptahydrate formulations.

EXAMPLE 16

Dissolution Study

An in vitro dissolution study was performed on pemirolast potassium (obtained Chemtronica AB, Stockholm, Sweden) and pemirolast sodium hemihydrate (prepared in accordance with the method described in Example 10 above) using standard Ph. Eur. Methodology (Apparatus 2 (paddle), Ph. Eur., 2.9.3, using 50 mM phosphate buffer pH 6.8 as a dissolution medium. A stirring rate of 50 rpm was employed. The temperature was 37° C.).

Tests were performed in triplicate. 30 mg of each substance was added to separate vessels and the timer started. Sampling was at regular intervals using a 1 mL plastic syringe, depending on how quickly the substance appeared to dissolve (by visual inspection). The sample was filtered into HPLC vials using a small diameter filter.

The samples were analysed by reversed phase HPLC. Quantification of pemirolast was performed by means of UV detection.

Results

Figure 8:
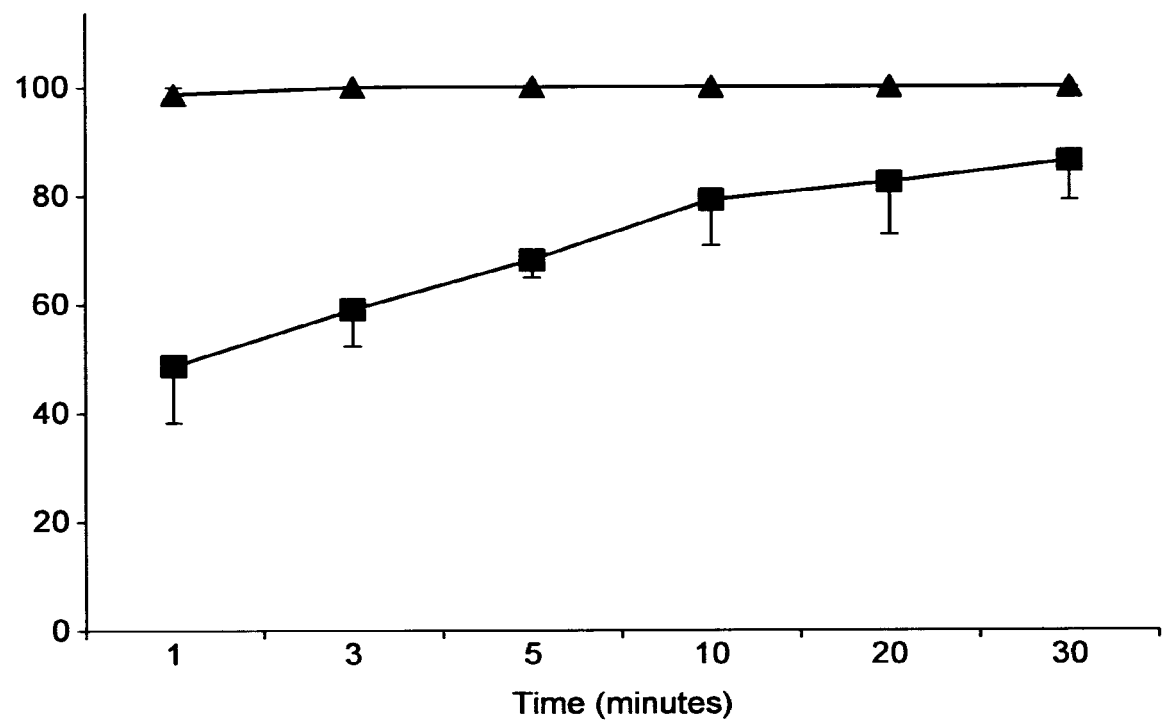
FIG. 8 shows a dissolution profile (percentage dissolution versus time) comparison between pemirolast sodium hemihydrate (squares) and pemirolast potassium (triangles); mean values ±SD (n=3 per group).

The potassium salt dissolved as soon as it was added to the dissolution medium whereas the sodium hemihydrate salt formed large aggregates and appeared to be more difficult to dissolve. The mean (±SD) of the three dissolution curves (percentage dissolved versus time) obtained for the two substances is shown in FIG. 8.

The invention claimed is:

1. A hemihydrate form of the sodium salt of pemirolast with 2-Theta values (in degrees) of 13.0±10%, 15.3±10%, 18.2±10%, 25.3±10%, 26.6±10%, and 28.4±10%.

2. A compound as claimed in claim 1, which is substantially crystalline.

3. A process for the preparation of a hemihydrate form of the sodium salt of claim 1, wherein the process comprises crystallisation from a solvent comprising a lower alkyl alcohol.

4. A process as claimed in claim 3 which further comprises reacting pemirolast with a sodium-containing base prior to the crystallisation.

5. A process as claimed in claim 4 wherein the base is sodium hydroxide or a sodium alkoxide.

6. A process as claimed in claim 3, wherein the lower alkyl alcohol is methanol or ethanol.

7. A process as claimed in claim 3, wherein the crystallisation comprises partial dissolution of pemirolast sodium in the solvent, in the presence of no more than about 10% (w/w, as a proportion of the solvent) of water.

8. A process as claimed in claim 7, which is carried out at a temperature of less than about 70° C.

9. A process as claimed in claim 3, wherein the crystallisation comprises partial dissolution of pemirolast sodium in an aqueous lower alkyl alcohol at about 72° C. or above.

10. A process for the preparation of a compound as claimed in claim 1, which comprises dehydration of a higher hydrate of pemirolast sodium.

11. A pharmaceutical formulation comprising a compound as claimed in claim 1 in admixture with a pharmaceutically acceptable adjuvant, diluent or carrier.

12. A combination product comprising:
  (a) a compound as defined in claim 1; and
  (b) one or more active ingredient that is useful in the treatment of an inflammatory disorder, or a pharmaceutically-acceptable salt or solvate thereof.

13. A compound according to claim 1 which is substantially crystallographically pure.

* * * * *